(12) United States Patent
Roecken et al.

(10) Patent No.: US 10,046,029 B2
(45) Date of Patent: Aug. 14, 2018

(54) METHOD OF INDUCING SENESCENCE IN TUMOR CELLS BY ADMINISTRATING TNF-A IN COMBINATION WITH IFNA OR IFNY

(71) Applicant: Martin Roecken, Tuebingen (DE)

(72) Inventors: Martin Roecken, Tuebingen (DE); Thomas Wieder, Dusslingen (DE); Matthias Hahn, Tuebingen (DE); Ellen Brenner, Tuebingen (DE); Heidi Braumueller, Tuebingen (DE); Killian Braungart, Tuebingen (DE); Sonja Assmann, Tuebingen (DE)

(73) Assignee: Martin Roecken, Tuebingen (DE)

( * ) Notice: Subject to any disclaimer, the term of this patent is extended or adjusted under 35 U.S.C. 154(b) by 0 days.

(21) Appl. No.: 14/651,267

(22) PCT Filed: Dec. 10, 2013

(86) PCT No.: PCT/DE2013/000794
§ 371 (c)(1),
(2) Date: Jun. 11, 2015

(87) PCT Pub. No.: WO2014/090224
PCT Pub. Date: Jun. 19, 2014

(65) Prior Publication Data
US 2015/0343024 A1    Dec. 3, 2015

(30) Foreign Application Priority Data

Dec. 11, 2012  (DE) .................. 10 2012 024 749

(51) Int. Cl.
| | | |
|---|---|---|
| *A61K 38/19* | (2006.01) | |
| *A61K 38/21* | (2006.01) | |
| *G01N 33/50* | (2006.01) | |
| *A61K 45/06* | (2006.01) | |
| *A61K 39/395* | (2006.01) | |
| *C07K 16/28* | (2006.01) | |
| *A61K 39/00* | (2006.01) | |

(52) U.S. Cl.
CPC .......... *A61K 38/191* (2013.01); *A61K 38/212* (2013.01); *A61K 38/217* (2013.01); *A61K 39/39541* (2013.01); *A61K 45/06* (2013.01); *C07K 16/28* (2013.01); *C07K 16/2866* (2013.01); *C07K 16/2878* (2013.01); *G01N 33/5011* (2013.01); *A61K 2039/507* (2013.01)

(58) Field of Classification Search
None
See application file for complete search history.

(56) References Cited

U.S. PATENT DOCUMENTS 4,650,674 A  *  3/1987  Aggarwal ............ C07K 14/525
                                            424/85.4
2012/0258117 A1    10/2012  Xu

FOREIGN PATENT DOCUMENTS

| EP | 0131789 | 6/1984 |
| EP | 0131789 | 1/1985 |
| EP | 0170843 | 2/1986 |
| WO | 2005007086 A2 | 1/2005 |
| WO | 2010/132867 A1 | 11/2010 |

OTHER PUBLICATIONS

Romagosa et al., Oncogene 30:2087-2097, 2011.*
Schmitt et al. (A senescence program controlled by p53 and p16ink4a contributes to the outcome of cancer therapy. Cell, 109, 335-346, 2002. (Year: 2002).*
Richard J. Gilbertson, "Resolving the stem-cell debate", Nature, vol. 488, Aug. 23, 2012, pp. 462-463.
Koebel, et al., "Adaptive immunity maintains occult cancer in an equilibrium state", Nature, vol. 450 Dec. 6, 2007, pp. 903-908.
Chen et al., "A restricted cell population propagates glioblastoma growth after chemotherapy", Nature, vol. 488, Aug. 23, 2012, pp. 522-527.
Gregory Driessens et al., "Defining themode of tumourgrowthby clonal analysis" Nature, vol. 488, Aug. 23, 2012, pp. 527-531.
Schreiber et al., "Cancer Immunoediting: Integrating Immunity's Roles in Cancer Suppression and Promotion", Science 331, 1565 (2011) pp. 1565-1570.
R. L. Marquet et al: "Anti-tumor activity of recombinant mouse tumor necrosis factor (TNF) on colon cancer in rats is promoted by recombinant rat interferon gamma; toxicity is reduced by indomethacin", International Journal of Cancer, Bd. 40, Nr. 4, Oct. 15, 1987 (Oct. 15, 1987).
Braumueller Heidi et al: "T-helper-1-cell cytokines drive cancer into senescence", Nature (London), Bd. 494, Nr. 7437, Feb. 2013 (Feb. 2013), pp. 361-365.
Vijaya Chaturvedi et al: "Role of INK4a/Arf Locus-Encoded Senescent Checkpoints Activated in Normal and Psoriatic Keratinocytes", The American Journal of Pathology, Bd. 162, Nr. 1, Jan. 1, 2003 (Jan. 1, 2003), pp. 161-170.

(Continued)

*Primary Examiner* — Elly-Gerald Stoica
(74) *Attorney, Agent, or Firm* — Stuart H. Mayer; Mayer & Williams PC

(57) ABSTRACT

The present invention relates to a combination of at least two different substances, one of which activates the STAT1-signalling cascade and the other of which activates the TNFR1/CD95-signalling cascade in order to induce permanent growth arrest—i.e. senescence—in pre-malignant or malignant tumors or tumor cells. This induction of permanent growth arrest does not depend on cytotoxicity and does not primarily attempt to kill tumor cells, although this may occur. The induction serves to treat and/or prevent tumors by permanent growth arrest. The combination is used for therapeutic or preventative senescence induction in tumors, in which the STAT1- and TNFR1/CD95-signalling cascade can be activated and in which p16lnk4a is present. The invention transfers tumor cells and, contrary to many other therapies, the tumor stem cells, into permanent growth arrest.

9 Claims, 17 Drawing Sheets

(56) References Cited

OTHER PUBLICATIONS

Wieder et al., "43rd Annual Meeting of the Arbeitsgemeninschaft Dermatologische Forschung e.v.,", Mar. 12, 2016, 1 page.
Wieder, et al. "Interferon-alpha-based immunotherapy induces senescence in human cancer cells in vivo", 1 page.

* cited by examiner

Figure 3
A
Control
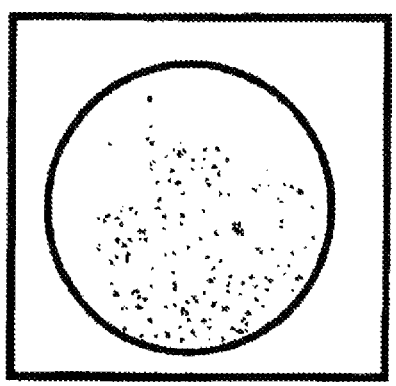
IFN-γ
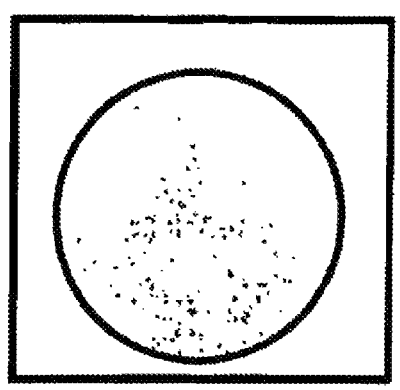
TNF
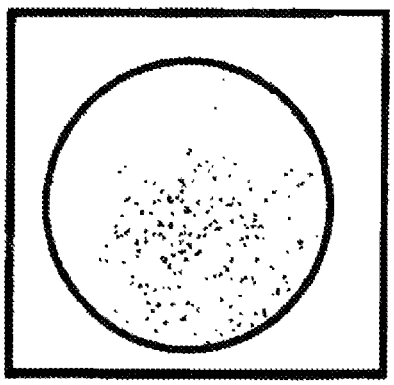
IFN-γ + TNF
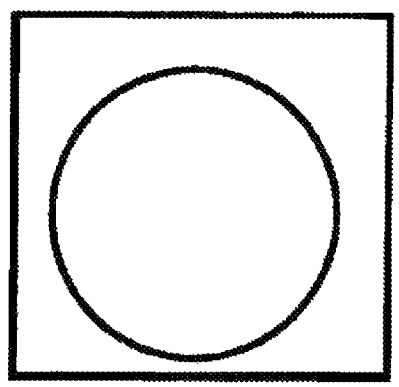
B
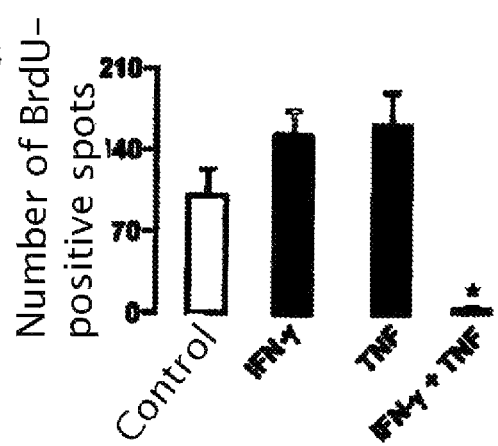

Figure 10

Table 1: Expression of cytokine receptors, and STAT1– and TNFR1–
dependent growth arrest in mouse cell lines.

| Cell line | IFNGR1 | IFNGR2 | TNFRSF1 | Inhibition of proliferation (%) | Growth arrest (%) |
|---|---|---|---|---|---|
| PyVmT Breast cancer | + | + | + | 75 ± 19 | 100 ± 29 |
| STAT1⁻/⁻ xRIP1-Tag2 Islet cell cancer | + | + | + | 26 ± 9 | 13 ± 4 |
| TNFR1⁻/⁻ xRIP1-Tag2 Islet cell cancer | + | + | – | | No growth arrest* |
| RIP1-Tag2 Islet cell cancer | + | + | + | 100 ± 32 | 100 ± 30 |
| LLC Lung cancer | + | + | + | 72 ± 24 | 100 ± 38 |

*strong in vivo growth

Figure 11

Table 2: Expression of cytokine receptors, and STAT1- and TNFR1-dependent growth arrest in 6 human cell lines.

| Cell line | IFNGR1 | IFNGR2 | TNFRSF1 | Inhibition of proliferation (%) | Growth arrest (%) |
|---|---|---|---|---|---|
| HOP-62 Lung cancer | + | + | + | 92 ± 24 | 100 ± 33 |
| COLO-205 Colon cancer | + | + | + | 96 ± 26 | 100 ± 35 |
| OVCAR-5 Cervical cancer | + | + | + | 98 ± 36 | 100 ± 33 |
| MALME-3M Melanoma | + | + | + | 100 ± 29 | 100 ± 22 |
| SNB-75 Brain tumor | + | + | + | 97 ± 41 | 100 ± 20 |
| SF-295 Brain tumor | + | + | + | 95 ± 36 | 100 ± 44 |

Figure 12

Table 3: STAT1- and TNFR1-dependent growth arrest
in 6 primary human cancer cell preparations.

| Internal code | Type of cancer and origin | Number of passages | Inhibition of proliferation (%) | Growth arrest (%) |
|---|---|---|---|---|
| SRH | Embryonic rhabdomyosarcoma | 6 | 36 | 100 |
| ZCRH | Alveolar rhabdomyosarcoma | 5 | 100 | >100* |
| T0Mel75 | Melanoma lung | 2 | 94 ± 13 | 100 ± 34 |
| T0Mel74H | Melanoma brain | 1 | 100 ± 40 | >100* |
| Z0Mel1H | Melanoma brain | 50 | 85 ± 17 | 88 ± 16 |
| Z0Mel1 | Melanoma lymph nodes | 50 | 89 ± 13 | 100 ± 12 |

* growth arrest combined with cytotoxic effects

Figure 13
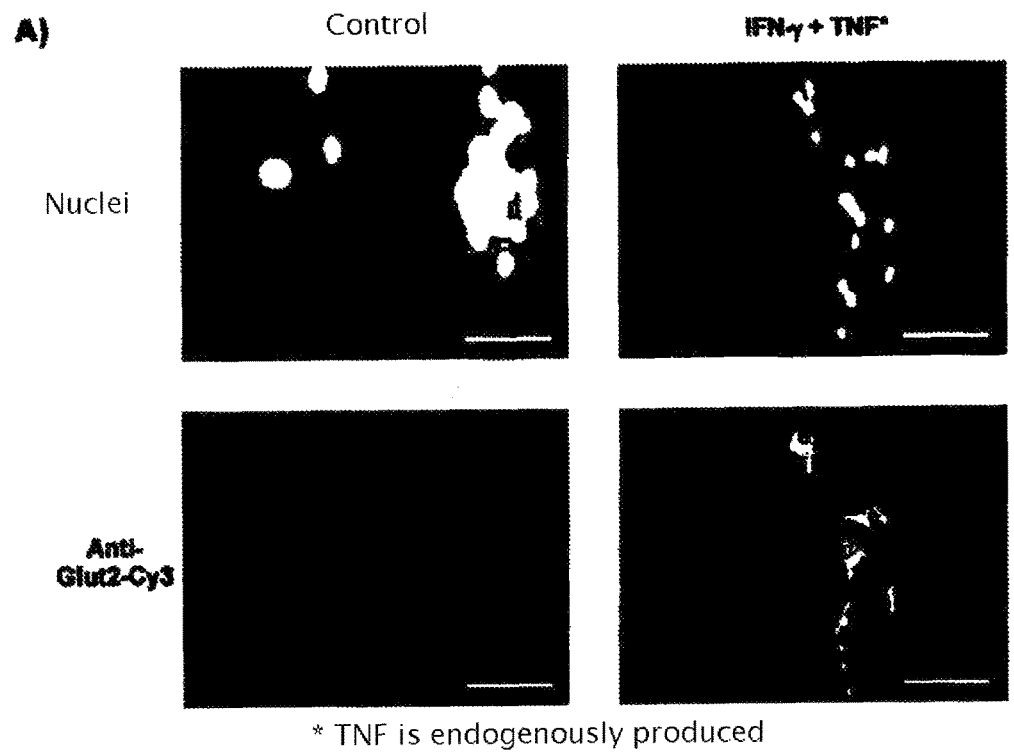
* TNF is endogenously produced
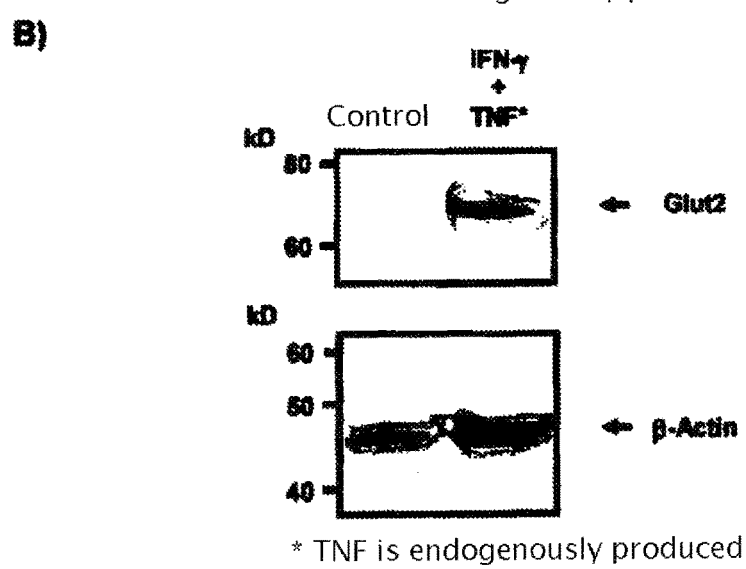
* TNF is endogenously produced Isolation of adherent tumor cell lines
p16Ink4a/Ki67 analysis of the p1
cell population in absence of IFN-α

METHOD OF INDUCING SENESCENCE IN TUMOR CELLS BY ADMINISTRATING TNF-A IN COMBINATION WITH IFNA OR IFNY

BACKGROUND OF THE INVENTION

The present invention relates to a combination of substances and to the use thereof for treating a tumor by induction of a tumor senescence.

In spite of many different approaches in the last decades, a successful tumor prevention and therapy is still a big challenge in science and medicine. Usually, nowadays, tumor therapies are performed by a surgical removal of the tumor, by means of irradiation, in which case normally ionizing radiation is used, and/or of a chemotherapy. The therapies are also combined. Latest therapies are based on the interaction of drugs with signaling cascades that help the tumors to undergo a pathological proliferation. It is important that all therapies developed up to now usually work only during the therapy application. Various data suggest that none of the therapies available up to now is able to fully eradicate tumors. For this reason, tumors tend to relapse, presumably starting from tumor stem cells (Ref. Nature 2012).

Further, cancer immunotherapies have been developed, in the context of which the respective patient is inoculated with surface antigens being specific for the tumor, with the aim to initiate immune responses, i.e. to kill the tumor cells through cytotoxic CD8 T lymphocytes, also called 'killer cells'. In still other therapy approaches, immune modulators are used, by means of which the patient's immune system is stimulated such that endogenous defense mechanisms are restored/activated such that they can destroy/kill the tumor. In these therapies, by the activation of endogenous or—in the case of the allergenic bone marrow transplantation—exogenous immune response, the malignant tumor cells destroyed; in most cases, a non-specific activation of the immune system occurs, or the transfer of tumor-specific cytotoxic lymphocytes occurs. Natural killer cells are also used. It applies for these applications, too, that many of the therapies work only during the therapy application, since in the rarest cases they will lead to a complete tumor eradication. Again, the tumors tend to relapse, presumably starting from tumor stem cells.

The role of the immune system during the tumor development has been examined in recent papers: Under certain circumstances, a state of equilibrium can be achieved, so that the development of new tumor cells and the destruction of existing tumor cells will temporarily lead to a standstill of the tumor growth (Koebel et al., Nature 450, 903 (2007); Schreiber et al., Science 331, 1565 (2011)).

Given this background, the efficient control of the tumor stem cells and the efficient inhibition of an exponential growth of the tumor cells by endogenous defense mechanisms is a big challenge for the treating physicians. In spite of the induction of strong, endogenous defense mechanisms that lead to a tumor reduction, in most cases they tend to re-start after completion of the therapy and re-grow after completion of the therapy. Further problems are caused by the drugs, which induce a non-specific immune activation, as their administration is associated with severe side effects. To date, it is assumed that the arrest of the tumor growth by the immune system, provided it occurs, is primarily based on that the immune response accelerates the tumor cell destruction such that an equilibrium between the tumor cell destruction and the natural tumor cell proliferation exists.

Given this background, it is the object of the present invention to provide a novel therapy approach being complementary to the previous therapy approaches oriented toward cytotoxicity, by means of which the development, the formation, and the growth of tumors can efficiently be treated or even prevented. This therapy is based on that the growth and the proliferation of tumor cells—including the tumor stem cells—are arrested in the long term.

SUMMARY OF THE INVENTION

According to the invention, this object is achieved by the use of a combination of at least two different substances, one of which activates the STAT1 signaling chain and the other one activates the molecules of the TNFR1 signaling chain or of the CD95 signaling chain, for the treatment and/or prevention of tumors by induction of a permanent growth arrest (senescence), wherein the substances that activate, on the one hand, the STAT1 signaling pathway and, on the other hand, the TNFR1/CD95 signaling pathway, are coupled to each other or are administered as single substances. In particular, they serve for the treatment and prevention of tumors, in which $p16^{Ink4a}$ is present.

Subject matter of the present invention is therefore the use of a combination of at least two different substances, one of which activates the STAT1 signaling chain, and the other one activates the TNFR1 signaling chain or the CD95 signaling pathway, for inducing a senescence in tumor cells. The invention further relates to the treatment and/or prevention of tumors by induction of a permanent growth arrest (senescence). This also applies to tumors that cannot be killed, i.e. wherein by a therapy (e.g., chemotherapy or immunotherapy) no cytotoxicity against the tumors can be initiated.

STAT1 ("signal transducers and activators of transcription" protein 1) is a transcription factor in human cells that as a regulatory protein as a signal transductor can directly transmit signals of receptors in the cell membrane to the potential promoters of the target genes in the cell nucleus. After stimulation with extracellular substances/cytokines or after the binding thereof to receptors, in particular interferon receptors, the STAT1 proteins are in turn activated themselves through the signal peptide receptors activated by extracellular substances by extracellular kinases. This occurs by a phosphorylation of tyrosine residues of the STAT1 proteins. By the dimerization caused thereby of the STAT monomers, the STAT dimers are transported into the cell nucleus, where the dimers bind to specific promoter sequences and can initiate the gene transcription. Receptors that are involved in the STAT1 signaling pathway, are, e.g., the interferon receptors type I and type II (TFNR1 and/or TFNR2), but also others such as epidermal growth factor (EGF) receptor and platelet-derived growth factor (PDGF) receptor; alternatively, the activation may also take place through hormones. Therefore, by selecting substances that bind to these receptors, the STAT1 signaling pathway can be activated, which according to the invention, in combination with the influencing of the TNFR1/CD95 signaling pathway, will lead to an efficient tumor treatment or prevention.

Accordingly, the "STAT1 signaling pathway" is understood here as the signaling pathway described in the above paragraph.

Substances that activate the STAT1 signaling chain, are, for instance, interferon-gamma (IFN-γ), interferon-alpha (IFN-α), anti-IFNR1 antibodies, anti-IFNR2 antibodies.

TNFR1 (also known as p55, CD120A) is one of the two receptors for cytokines of the TNF family, in particular tumor necrosis factor (TNF-α, TNF) and lymphotoxin (LT). TNF-α offers, after binding to the TNFR1 in the cell, a wide spectrum of effects, such as inflammations, apoptosis and necrosis. Thus, via the TNFR1—according to previous findings—either cell death (apoptosis) or inflammation can be mediated. An inhibition of the TNFR1 signaling cascade, therefore, is used today, for instance, for the treatment of inflammatory autoimmune diseases such as psoriasis. TNFR1 is part of a signaling chain family. CD95 and TNFR1 have a substantially identical intracellular signaling chain with substantially overlapping signaling pathways.

TNFR1 is, as is CD95, a transmembrane protein with an extracellular ligand binding domain and extracellular cysteine-rich domains that are responsible for the ligand specificity, inter alia. When TNF-α binds to TNFR1, thereby a conformational change of the receptors having been inactive before is initiated, whereby again different intracellular signaling molecules, such as, e.g., TRADD or the serine kinase RIP and indirectly the tumor necrosis factor receptor associated factors (TRAFs), can bind to the receptor and can be activated thereby. By binding of TNFR1-specific ligands/substances to TNFR1, thus, this TNFR1 signaling pathway can be triggered. Very similar intracellular, for the most part identical signaling pathways can be activated by binding of CD95.

Substances that activate the TNFR1 signaling chain or the CD95 signaling pathway, are, for instance, tumor necrosis factor-alpha (TNF-α), anti-TNFR receptor 1 antibodies, anti-CD95 antibodies.

An TNFR1 activation in combination with the targeted activation of the STAT1 signaling pathways thus causes according to the invention an unexpected effect in individual tumor cells as well as in complete tumors. The common/coordinated activation of these two signaling pathways leads to a new signal quality that has not been observed or described up to now: Commonly, the activation of the two signaling pathways leads to that the tumors, in which the two signaling pathways can be activated, are transferred into a permanent growth arrest: i.e. the tumor cells are not killed, bus lose their capability of behaving like tumor cells. In the tumor cells is induced the state of the permanent growth arrest, also called senescence. The induction of this growth arrest is used, according to the invention, for tumor prevention and tumor therapy. Due to the substantially identical intracellular signaling cascades, an activation of CD95 and STAT1 can also induce a senescence.

Accordingly, the "TNFR1 signaling pathway" is understood here as the signaling pathways described in the above paragraph.

Further, "tumor necrosis factor" is abbreviated by TNF and used alternately, however with the same meaning. Interferons type I and type II are correspondingly abbreviated by "IFN" and used with the same meaning.

Subject matter of the invention is, therefore, the use of a combination of at least two different substances, one of which activates the STAT1 signaling chain, and the other one activates the TNFR1 signaling chain or the CD95 signaling pathway, for inducing a senescence in tumor cells, in particular in premalignant or malignant, bona fide tumor cells/tumors and tumor stem cells.

A preferred subject matter of the invention is, therefore, the use of a combination of active substances, comprising at least one substance selected from the group "interferon-gamma (IFN-γ), interferon-alpha (IFN-α), anti-IFNR1 antibodies, IFNR2 antibodies" and a second substance, selected from the group "tumor necrosis factor-alpha (TNF-α), anti-TNF receptor 1 antibodies, anti-CD95 antibodies". When using antibodies, such as, e.g., anti-IFNR1 antibodies, anti-IFNR2 antibodies, anti-TNF receptor 1 antibodies, anti-CD95 antibodies, care has to be taken that these must act agonistically, i.e. that they must lead to the stimulation of the receptor.

A particularly preferred subject matter of the invention is the use of a combination of interferon-gamma (IFN-γ) with tumor necrosis factor-alpha (TNF-α) or of a combination of interferon-alpha (IFN-α) with tumor necrosis factor-alpha (TNF-α).

Herein, the terms "tumor" and tumor cell" are also synonymously used with "cancer" or "cancer cell" or "malignant" cell, "malignoma", i.e. are intended to mean the same. The term "induction of a senescence in tumor cells" comprises, in the meaning of this application, all known tumor cell types, including premalignant or malignant, bona fide tumor cells/tumors and tumor stem cells.

Cytokines binding to TNF receptors as well as binding to STAT1-dependent receptors (i.e., e.g., TNF-α and interferon-γ) are used today already as single substances for tumor therapy, such as, e.g., disclosed in the EP 0 170 843 or the EP 0 1317892, however, the previous therapy approaches, including those that refer to this patent protection, had experimentally as well as therapeutically disappointingly to strongly limited effects. A therapeutic effect of these single substances exceeding killing tumor cells (cytotoxicity) or inhibiting growth of new blood vessels (anti-angiogenesis), could not be shown; no long-term therapeutic effects could be achieved. The finding that by the combined activation of the STAT1 and the TNFR1 or CD95 signaling chains substances, also besides TNF and interferon-γ, can be used and screened specifically for the treatment of tumors, was not known in prior art.

In particular, it could not be found in prior art that the state of senescence of tumor cells is possible by induction, i.e. by the application of IFN and TNF or substances that activate the STAT1 and TNFR1/CD95 signaling pathway. In previous patents such as EP 0 170 843 or EP 0 1317892, it was disclosed that by the combination of TNF and IFN, tumor cells are killed by necrosis or apoptosis. By patented and previously known methods and test methods, only the killing of tumor cells could be detected. Since killing never covers 100% of the cells, the tumors will regenerate from the surviving tumor cells and stem cells and will then again grow in an uninhibited manner. The surviving tumor cells and the tumor stem cells pose a problem, since the tumors will regenerate from them (Nature 2012). The invention presented here clearly shows that with the two previously approved patents, an efficient tumor therapy can neither be performed nor planned. For A) IFN and TNF may cause a cytotoxicity in many tumors and kill them in vitro and in vivo—therefore the name tumor necrosis factor. However, killing will not lead to senescence in all tumors, and the previously described analysis methods (Pat I and Pat II) do also not allow detecting senescent tumor cells, not even accidentally. The methods do also not allow finding out, whether tumor stem cells are arrested. Our data have clearly shown, however, that a therapy is only then efficient on a long-term basis, when the tumor cells as well as the tumor stem cells come into a permanent growth arrest.

B) Numerous tumors cannot be killed by the combination of TNF and IFN. But they are brought by the combined action of IFN and TNF into a permanent growth arrest, the senescence. The invention presented here shows that only this long-term growth arrest that is also independent from killing, protects against tumors; this is completely independent from whether or not the tumors are also killed by the combined activation of the TNFR1 and of the STAT1 pathways.

The inventors of the present invention have now developed, in own examinations, an approach that allows to induce in tumors a therapeutically effective permanent sleep state or growth arrest (here and in the respective field also called senescence). Thereby, for the first time, an immunotherapeutic approach is provided, by means of which already malignant tumors can be transferred into senescence, i.e. a permanent cell cycle arrest.

It is crucial, herein, that the therapy approach induces, through signaling molecules that are responding to cytokines, a stable and permanent growth arrest in the tumor cells, i.e. a tumor cell senescence. It is important that the growth arrest also extends far beyond the actual direct time of action of the inductors/substances. This concept of the immunotherapy was previously not known as a therapy measure, or has not been employed.

This approach is based, as already described above, to activate in a specific manner the combined effect of substances, which activate the STAT1 and TNFR1 signaling chains. According to the invention, the substances can be used separately from each other or coupled to each other; by "coupled" it is understood that the substances are connected to each other either chemically, recombinantly, or functionally; by this coupling, a bispecificity can be achieved.

Subject matter of the present invention is, therefore, also the use of a combination of at least two different substances, one of which activates the STAT1 signaling chain, and the other one activates the TNFR1 signaling chain or the CD95 signaling pathway, for inducing a senescence in tumor cells, in particular in premalignant or malignant, bona fide tumor cells/tumors and tumor stem cells, wherein the substances, one of which activates the STAT1 signaling chain, and the other one activates the TNFR1 signaling chain or the CD95 signaling pathway, can also be used in a coupled manner.

The use according to the invention of the combination leads to an induction of the endogenous kinase inhibitor $p16^{Ink4a}$, by means of which the cell cycle-regulating retinoblastoma (Rb) is hypophosphorylated, and thus a signaling cascade is initiated that arrests the cell cycle. Thereby, tumors can also be treated and transferred into the permanent quiescent state, wherein, by viral gene modifications or so-called "tumor driver" mutations exactly this signaling cascade is disturbed. Only the combined activation of the STAT1 and of the TNFR1 signaling pathway or the combination of substances that activate these two intracellular signaling pathways, is effective—and this has been shown by the inventors in own experiments. In contrast, surprisingly, the single administration of the substances is not effective. Neither the activation of TNFR1 alone nor that of STAT1 alone can induce a permanent growth arrest, i.e. a senescence. At most, they can slow down the growth of tumor cells—this is however completely different from the state of senescence. This has clearly been shown by experiments. Only the combined administration of IFN and TNF, and thus the combined activation of the STAT1 and TNFR1 signaling cascades can induce the senescence. It is crucial that the senescence is induced in tumor stem cells, too.

The inventors could show in so-called "RIP1-Tag2" mice, in which the large T antigen (Tag) causes cancer by attenuation of the p53- and Rb-mediated cell cycle control, that by the common activation of STAT1 and TNFR1 these tumors are transferred into the quiescent state, by that this common activation induces a permanent growth arrest in the $G_1/G_0$ phase. They show that the common activation of STAT1 and TNFR1, and only the common activation of STAT1 and TNFR1, leads to an increase of the $p16^{Ink4a}$ protein, whereby Rb is present in the hypophosphorylated state and thus then E2F2 genes are suppressed.

It was previously neither known nor described that messenger substances such as cytokines, e.g., interferons or TNF, antibodies or other exogenous or endogenous substances can trigger a permanent growth arrest in tumor cells. The latter is only known for a few chemotherapeutics, the administration of which is associated with strong side effects.

However, the inventors could additionally show three more crucial aspects that highlight the novelty of the approach: The induction of the senescence through the activation of STAT1 and TNFR1 in tumors in vivo leads to that the tumor cells cannot grow anymore, even when they are isolated from the treated animals and thus there is no direct treatment anymore. Even when they are then transplanted into severely immunodeficient mice, they will not grow anymore. They behave as truly benign cells (in spite of the contained tumor gene); tumor stem cells can also be permanently arrested by the induction of senescence. Further, the inventors could show by genetic analyses by means of chromosomal gene hybridization that the induction of senescence by STAT1 and TNFR1 stabilizes the genome of the tumor cells and their potential forerunners. Further, it has been shown that the activation of STAT1 and TNFR1 induces a senescence also for other tumors of the mouse serving as a model for tumors of the human; further, it has been shown for 6 different tumor cell lines and several freshly isolated tumors of man shown that this also applies to tumors of the human.

In a conventional way, the cell cycle is subdivided into four sections, namely the $G_1$ phase, the S phase, the $G_2$ phase, and the M phase. In the $G_1$ phase, the preparation for the DNA replication occurs, in the following S phase mainly the DNA is duplicated and other important cell constituents such as, e.g., phospholipids are synthesized, in the following $G_2$ phase the integrity of the genomes is checked and the cell division is prepared, and in the final mitotic (M) Phase the duplicated genome is uniformly distributed to the daughter cells. Before beginning the next $G_1$ phase, the cells can leave the described cell cycle and enter into the so-called quiescent phase ($G_0$), in which they are removed from the cell cycle by differentiation. The $G_0$ phase is reversible, and the cells can return into the $G_1$ phase by certain mitosis-triggering signals, such as, e.g., growth factors, tumor viruses, and can then participate in the cell cycle.

In the $G_0$ and $G_2$ phases, DNA repairs are possible that ensure the genetic integrity of the cell and protect the latter from an uncontrolled proliferation. Proteins such as Rb (retinoblastoma) and p53 enable the transition into this quiescent phase. Disturbances and mutations in the area of the p53 or Rb signaling cascade will lead to an uncontrolled cell proliferation and furthermore in the long term to malignant tumors. In the control of the cell cycle are further involved, among others, cyclin-dependent kinases (CDK 1-8) and their inhibitors (CDKIs), by that they form complexes with respectively specific cyclins.

Two different protein families, among others, have an inhibitory effect in the cell cycle: members of the $p16^{Ink4}$ family inhibit CyklinD/CDK4/CDK6 complexes in the early S phase, and molecules of the P21 cip/waf family are acting in the late $G_1$ phase. They act as counterregulators of the above system and inhibit the cellular proliferation. If these negative regulators fail, e.g., by mutation or deletion of the genes or by a disturbed gene expression, a malignant degeneration of the cells will be caused.

The regulation of the cell cycle occurs, as mentioned above, by the cyclin-dependent kinases (CDKs) and different cyclins that at defined times associate with different kinase subunits in the cell cycle, whereby a network of kinase activities is created that regulates the course of the cell cycle by controlled phosphorylation of target proteins. Among others, by the phosphorylation of the retinoblastoma protein (Rb protein) that blocks the transcription factor E2F2 in an unphosphorylated manner, E2F2 is liberated, whereby this transcription factor can activate genes of the cell cycle.

By means of the senescence marker "phosphorylated heterochromatin protein 1γ" PHP1γ or the senescence-associated β-galactosidase (SA-β-gal) it has been shown that actually by the simultaneous activation of STAT1 and TNFR1 a more stable growth arrest could be induced, i.e. the entry of the tumor cells into the $G_0$ phase. This was confirmed by cell cycle analyses; only after the combined activation of the STAT1 and TNFR1 signaling pathways, the tumor cells left the S phase and built up in the $G_0$ phase.

Further, by the combined use of two substances that activate the STAT1 or the TNFR1 signaling pathway, a permanent growth arrest of β-cancer cells can be achieved, whereas the activation either of the one or of the other signaling cascade can slow down the cell growth, but can by no means induce a complete and in particular permanent growth arrest persisting beyond the application of the cytokines Experimentally, it could be shown that the permanent growth arrest (the senescence) induced in vivo remained stable over a plurality of months—as long as the experiment could be continued for time and technical reasons.

According to a preferred embodiment, the substances are selected from the group of the cytokines and activating antibodies that bind to the interferon receptors or TNFR1/CD95, soluble mediators such as mimetics, 'small molecules', hormones (e.g., progesteron) or intracellular signaling molecules that activate the STAT1 or TNFR1 signaling cascade, suppress STAT1 inhibitors, and "peptidomimetics" that imitate the effect of TNF, CD95 ligands, or IFN. siRNA- or shRNA-based suppression of endogenous inhibitors of the TNFR1 or STAT1 signaling cascade is also an approach.

Substances to be used according to the invention include activated T cells, in particular $T_H1$ cells, these being activatable either exogenously or endogenously, e.g., by interleukin-12 and interferon-α. The activated T cells, in turn, secrete interferon-γ and TNF and can thus trigger the signaling cascade described above.

According to the invention, the one of the substances to be used in the combination activates the STAT1 signaling chain, and the other substance to be used in combination activates the TNFR1 signaling chain, preferably cytokines, but also activating antibodies, peptidomimetics or hormones being used that bind to the two receptors, and thus activate both signaling chains. Alternatively, antibodies, immunostimulants, such as TLR ligands or stimulators of the endogenous signal recognition, (e.g. immunostimulatory DNA motifs), or other immunotherapeutics are used that stimulate the endogenous cytokine production such that thereby the STAT1 and the TNFR1 signaling pathways can commonly efficiently be activated.

In further embodiments, it may be provided to bring the substances by means of immune cells, DNA/RNA small particles, nanoparticles, virotherapy or immunotherapy directly close to the tumors or into the tumor cells and thereby increase their efficient dose at the site of action.

According to the invention, there occurs no killing of the tumor (e.g., apoptosis, lysis, necrosis) or anti-angiogenesis, but a targeted growth arrest. In a preferred embodiment, the combination consists of TNF (tumor necrosis factor), CD95 ligands and interferon-γ. According to an alternative embodiment, the combination does not consist of TNF and interferon-γ.

According to the invention, alternative concentrations of the substances or of the combination are employed, by which it is not intended to achieve cell death (it may occur with this combination, but this is not the aim of the therapy and also not required therefor), but a permanent cell cycle arrest or the induction of senescence. Thereby, the tumors are stabilized in their genome, i.e., according to the invention, the genomic degeneration of the tumor cells and of their forerunners is inhibited. I.e., it is achieved, according to the invention, that the tumor cells keep or regain their normal functional differentiation. This was not the aim of the previous therapies directed to the killing of the tumor cells. By conventional therapies, it was even often achieved that the tumor cells phenotypically continued degenerating. The conventional immunotherapy approaches allowed neither to seek the aim of senescence nor to accidentally discover this aim by measurement.

Another subject matter of the invention is, therefore, the use of a combination of substances, one of which activates the STAT1 signaling chain, and the other one activates the TNFR1 signaling chain or the CD95 signaling pathway, for preventing the further degeneration of tumor cells. Another aspect of the invention is the use of a combination of substances, one of which activates the STAT1 signaling chain, and the other one activates the TNFR1 signaling chain or the CD95 signaling pathway, for regaining the functional differentiation of a tumor cell.

According to the invention, the combination is employed for tumors, wherein the STAT1 and TNFR1 signaling cascades are activatable and $p16^{Ink4a}$ is present. According to the invention, tumors with non-compensated deletion of the p21-p19-p16/p14AARF complex cannot be treated.

The tumor to be treated preferably is a tumor that can be transferred by the combined activation of the STAT1 signaling chain and of the TNFR1 signaling chain into a permanent quiescent state, and is preferably selected from tumors such as HPV-induced benign tumors, precanceroses and carcinomas, breast cancer, sarcomas, melanomas, carcinomas (ovaries, cervix, skin and mucosae, prostate, kidney, lung), CNS tumors or lymphomas/leukemias. According to the invention, the efficient activation of the TNFR1 and of the STAT1 signaling cascade is possible and $p16^{Ink4a}$ is functionally obtained; other frequent disturbances of the senescence signal cascade, such as an inhibition of p53 or Rb, for instance, by Tag, as it occurs in HPV-induced tumors, can be compensated especially by the efficient activation of STAT1 and TNFR1; this was experimentally proven by the inventors.

As experimentally shown by the inventors, a tumor cell can be transferred by contact with the combination of substances according to the invention in a concentration from 0.0001 ng/ml to 10,000 ng/ml into the state of senescence. As soon as the senescence has occurred, the cell remains in this state, even when the substances according to the invention are not further applied. This applies in particular also for tumor cells, wherein no cytotoxicity or apoptosis can be triggered by the combined action of IFN and TNF/CD95, and which cannot be killed by the combined activation of the TNFR1/CD95 and STAT1 signaling cascades.

For the purposes of the in vivo treatment, therefore, it has to be ensured that all tumor cells are transferred, according to the teaching of the present invention, into the state of senescence. The treatment, therefore, has to ensure that the substances according to the invention are achieved in the above range of concentrations at the site of action (i.e. at every individual tumor cell). This is ensured by that the treatment by the combination of substances according to the invention persists with a combination from 0.0001 ng/ml to 10,000 ng/ml over at least 3-4 days. If a patient has developed already tumors with a diameter of 5 mm or larger, then the treatment should be up to 30 days. In order to prevent that possibly individual cells were not transferred into the state of senescence (for instance, since no sufficient concentration of the combination of substances according to the invention was achieved at the site of action), the initial treatment can be repeated after a time of 3-6 weeks. A close observation of already formed tumors, if applicable, is recommended. If these continue to grow after the treatment with the combination of active substances according to the invention, the treatment according to the invention may also be performed by peritumoral or intratumoral application. In this way, it can be ensured that the necessary concentration of the active substance according to the invention is achieved at the site of action, namely at the individual tumor cell.

The present invention, therefore, also relates to a pharmaceutical composition comprising a combination of substances, one of which activates the STAT1 signaling cascade, and the other one activates the TNFR1/CD95 signaling cascade, for the treatment and/or prevention of tumors, wherein the substances may be present in the pharmaceutical composition as isolated single substances, in particular a pharmaceutical composition comprising at least one substance selected from the group "interferon-gamma (IFN-γ), interferon-alpha (IFN-α), anti-IFNR1 antibodies, anti-IFNR2 antibodies", and a second substance selected from the group "tumor necrosis factor-alpha (TNF-α), anti-TNF receptor 1 antibodies, anti-CD95 antibodies". When using antibodies, such as, e.g., anti-IFNR1 antibodies, anti-IFNR2 antibodies, anti-TNF receptor 1 antibodies, anti-CD95-antibodies, care has to be taken that these must act agonistically, i.e. that they must lead to the stimulation of the receptors.

A particularly preferred subject matter of the invention is a pharmaceutical composition comprising a combination of interferon-gamma (IFN-γ) with tumor necrosis factor-alpha (TNF-α) or a combination of interferon-alpha (IFN-α) with tumor necrosis factor-alpha (TNF-α).

According to a preferred embodiment, a combination of activating signaling molecules (such as cytokines or hormones) or antibodies is particularly preferred through which the above signal chains can be activated.

Further, it is preferred that according to an embodiment of the invention, the substances are each employed in a concentration from 0.0001 ng/ml to 10,000 ng/ml in the pharmaceutical composition at the site of action.

Besides the combination according to the invention, further auxiliaries, additives or excipients may be contained, which facilitate, simplify, or allow the respective administration.

In the context of the invention, the therapeutically effective or therapeutically efficient amount of the substances to be used in combination is that amount of the combination of at least two substances, as explained above, which can induce the senescence, i.e. the permanent quiescent state of the tumor. The exact efficient amount for a patient depends on the height and health state, the localization, the type and the extent of the tumor disease and the combination of the substances to be used in the pharmaceutical composition.

A patient can be administered the pharmaceutical composition in a variety of forms that are adjusted to the selected route of administration, namely parenteral, oral, intraperitoneal, transdermal etc. A parenteral administration includes the administration on the following routes: intravenously, intramuscularly, interstitially, intraarterially, subcutaneously, intrasynovially, transepithelially, including transdermally, pulmonally, olphtalmically sublingually and lybucally, topically including dermally, ocularly, rectally, and a nasal inhalation via insufflation, or peri-/intratumorally.

The administration can occur in the form of solutions, tinctures, ointments, powders, and suspensions, or of other liquid or solid formulations and as tablets, capsules, sprays, viruses, packed, bound or free DNA or RNA, nanoparticles, or cells such as T or NK cells.

As mentioned further above, the pharmaceutical composition may also include pharmaceutically acceptable excipients, binding agents, diluents, excipients, or adjuvants. The selection of a pharmaceutical carrier, excipient, or other adjuvant can be performed in view of the intended route of administration and the standardized pharmaceutical practice. Pharmaceutically acceptable excipients include solvents, cutting agents, or other liquid binding agents such as dispersion or suspension adjuvants, surface-active agents, isotonic active substances, masking agents or emulsifiers, preservation agents, enclosing agents, solid binders or lubricants, depending on what is best suitable for the respective dosage and is also compatible with the combination according to the invention. A survey of such additional ingredients can be found, e.g., in A. Kibbe: Handbook of Pharmaceutical Excipients, 3rd Edition, 2000, American Pharmaceutical Association and Pharmaceutical Press.

The pharmaceutical composition according to the invention may also include pharmaceutically acceptable salts, such as, e.g., salts of mineral acids, such as hydrochlorides, hydrobromides, phosphates, sulfates and the like; but also salts of organic acids.

As mentioned further above, a preferred therapeutic administration of the pharmaceutical composition is made, in the case of cytokines, in the range from 0.0001 ng/ml to 10,000 ng/ml in the pharmaceutical composition at the site of action, wherein a therapeutically efficient daily dose of the combination according to the invention must be achieved in the area of the existing or developing tumor, preferably 0.001 μg to 1000 mg/kg tumor tissue. When immunoactivating antibodies, or immunostimulatory molecules (such as immunostimulatory DNA motifs; exogenous or endogenous activation of the "innate immunity") are used, the dosage depends on the strength, with which an efficient T or NK cell activation occurs. Typically, the physician will determine the actual dose that is required for a certain patient, which will happen under consideration of the type of application, the patient's age, weight, and general state of health. The possible endogenous production of the active substances, for instance, of TNF-α will be taken into account: In tumors, in which the TNF-α is already endogenously formed in a sufficient amount, the addition of further TNF-α can be dispensed, if applicable.

In the context of the present application, the pharmacological induction of a senescence of tumor cells was described for the first time. Such an induction of the senescence for tumor cells had not been described before. The induction of senescence in particular also extends to tumors that cannot be killed by the combination of active substances and to tumor stem cells that seem to be resistant to nearly all other therapy approaches. The results described in the context of the present invention also allow, therefore, the establishment of a screening assay for investigating pharmaceutical substances for their ability of inducing such a senescence. Single substances, preferably however combinations of substances can be contacted with tumor cells, and the tumor cells can thereafter be investigated for whether the stage of senescence has been achieved. If yes, the single substances or combinations of substances can then be investigated for whether they are suitable pharmaceutical active substances. Subject matter of the present invention is, therefore, also a method for screening active substances and combinations of active substances for the induction of a senescence in tumor cells.

Another aspect of the present invention is the possibility to investigate the particular tumor type of a particular patient before the treatment for whether an active substance and, if applicable, which active substance or which combination of active substances is suitable to induce a senescence in this particular tumor type. For this purpose, a tissue sample of the patient (for instance, from a biopsy) can be subjected to the method described above. This means that isolated, single tumor cells are exposed to a combination of active substances and are then investigated for whether a senescence has been induced.

Subject matter of the invention is, therefore, also a method for testing tumors for the possibility of a treatment by pharmacologically induced senescence, characterized in that tumor cells are removed by biopsy, the isolated tumor cells are reacted for a period of time from 4 to 14 days with a solution containing the active substances to be examined in a concentration from 0.0001 ng/ml to 10,000 ng/ml, and then are examined for whether a senescence has occurred.

Further advantages result from the following description and the appended figures.

It is understood that the features mentioned above and also those to be explained in the following cannot only be used in the respectively mentioned combination, but also in other combinations or alone, without departing from the scope of the present invention.

EXAMPLES

The invention will be explained in more detail by the following examples that are not intended to be limiting.

BRIEF DESCRIPTION OF THE DRAWINGS

Some embodiments of the invention are shown in the figures and are explained in more detail in the following description. There are:

FIG. 3 shows the proof that only a combined activation of STAT1 and TNFR1 induces in vitro a stable growth arrest in isolated β-cancer cells, not however an activation of respectively only one of the two signaling pathways: FIG. 3A shows that by a treatment of β-cancer cells that were cultivated for 4 to 5 days either with medium (Co.), interferon-γ, TNF, or a combination of interferon-γ and TNF, only β cells that were treated with the combination, were transferred into the permanent quiescent state. FIG. B shows the number of BrdU-positive β-cancer cells after the treatment with medium (Co.), interferon-γ, TNF, or the combination of interferon-γ and the TNF, wherein at the time of the measurement the cytokines were removed from the medium since 2 weeks already.

FIG. 4A shows TNFR1-deficient β-cancer cells, the senescence cannot be induced by interferon-γ and TNF. FIG. 4B shows STAT1-deficient β-cancer cells, the senescence cannot be induced by interferon-γ and TNF.

FIG. 10 shows in Table 1 the proof for 3 tumors of the mouse that severe disturbances in the p53-Rb senescence cascade (such as the inhibition thereof in RIP-TAG or PyVmt tumors) could be compensated through the induction of senescence; furthermore is shown that the common activation of STAT1 and TNFR1 was necessary to induce the senescence, for the absence of one of the two signaling pathways had stopped again the induction of senescence in vivo and in vitro.

FIG. 11 shows the proof in 6 different tumor cell lines that the combined activation of STAT1 and TNFR1 induces a senescence in different tumors of the human.

FIG. 12 shows the proof in 4 different freshly isolated tumors of the human that the combined activation of STAT1 and TNFR1 induces a senescence in different tumors of the human.

FIG. 13A shows the proof by immunofluorescence that isolated, fully de-differentiated β-cancer cells re-differentiate again in presence of the $T_H1$-cytokines IFN-α and TNF to bona fide islet. FIG. 13B shows the proof by Western blot that isolated, fully de-differentiated β-cancer cells re-differentiate again in presence of the $T_H1$-cytokines IFN-α and TNF to bona fide islet.

FIG. 15 shows the result of a healing test of a patient having a peritoneal carcinoma with IFN-α and TNF: A strong induction of p16$^{Ink4a}$ occurs after treatment and a significant decrease of the proliferation marker Ki67. For proof of the cell, the cell nuclei were additionally stained with DAPI.

FIG. 16B shows a reduced proliferation rate. FIG. 16C shows a very high activity of the senescence-associated β-galactosidase (SA-β-gal), 16C). FIG. 16D shows a strong expression of p16$^{Ink4a}$ (16D).

DETAILED DESCRIPTION OF THE INVENTION

Figure 1A:
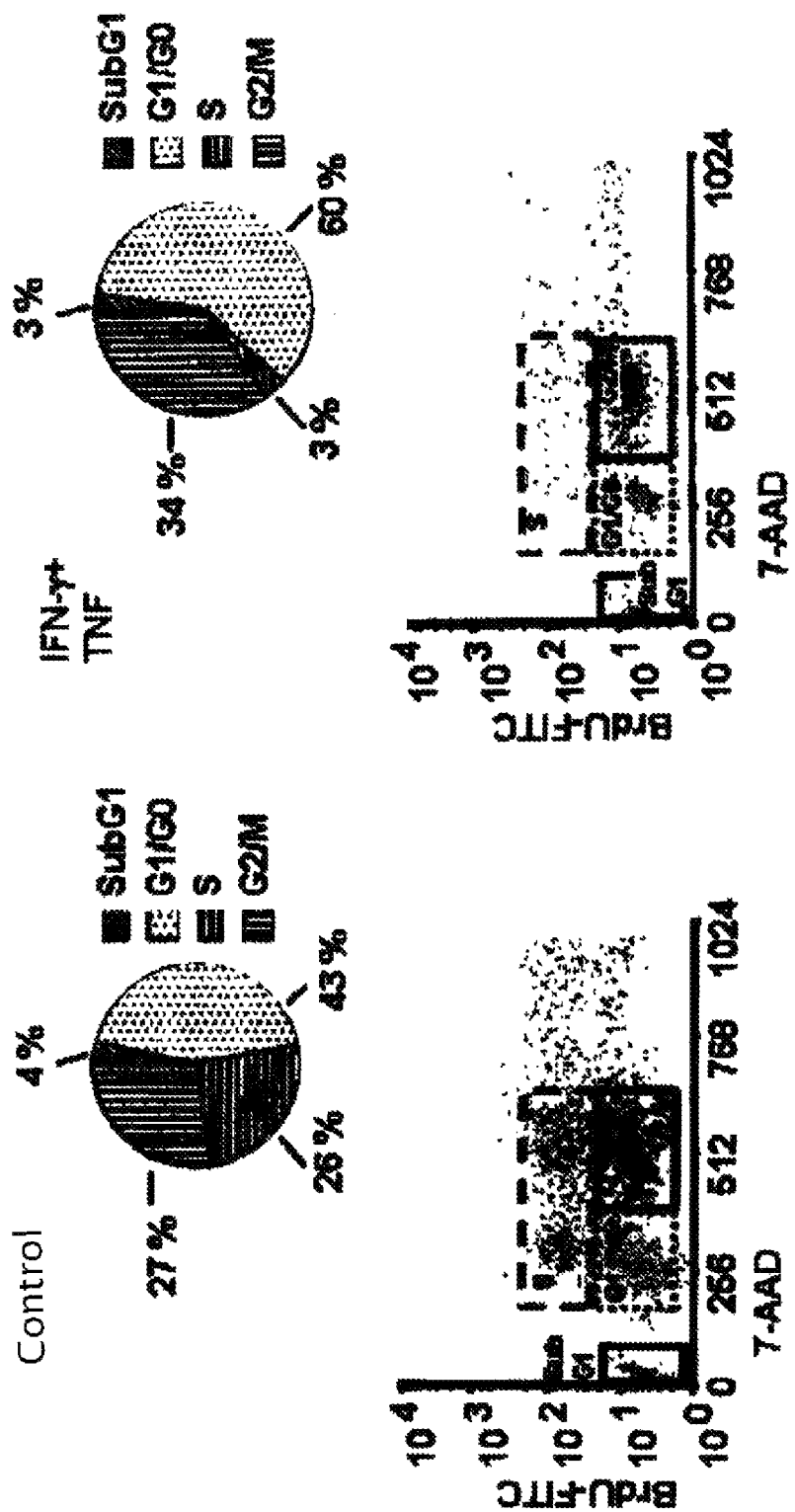
FIG. 1A shows a FACS plot and a diagram, from which can be taken that the combination of two substances, which activate the STAT1 and the TNFR1 signaling cascades (here: interferon-γ and TNF), arrested cancer cells in the $G_1/G_0$ phase, without killing them—there is no enrichment of the cells in the sub-$G_1$ phase (right-hand illustration).

Methods
Animals:

For the experiments, C3H mice (Charles River, Sulzberg, Germany), transgenic RIP1-Tag2 mice, double-transgenic TNFR1$^{-/-}$ and STAT1$^{-/-}$ mice were employed.
Cell Culture and Single Cell Analysis:

Tag-specific $T_H1$ cells were isolated and characterized by means of flow cytometry. Tumors were isolated from sham and RIP1-Tag2 mice treated with Tag-$T_H1$ cells, and from sham and TNFR1$^{-/-}$×RIP1-Tag2 mice treated with Tag-$T_H1$ cells, STAT1$^{-/-}$×RIP1-Tag2 mice or from transgenic breast cancer mice by means of collagenase digestion (10 min at 37° C.), and thereafter separated under a dissecting microscope. The tumor cells were obtained by incubation in 0.05% Trypsin/EDTA solution (10 min at 37° C.) and seeded on tissue culture plates. Adherent cells were cultivated for 2 to 5 weeks in RPMI 1640 medium, supplemented with 10% fetal calf serum, non-essential amino acids, antibiotics and 50 μM 2-mercaptoethanol, at 37° C. and 5% $CO_2$. The murine cancer cell lines B16, LLC and CT26 EpCam, and 11 human cancer cell lines from the NCI 60 panel[2], six primary human tumor cell preparations, and human rhabdomyosarcoma cells (A204 cells) were also cultivated in complete RPMI 1640 medium. Unless otherwise stated, the cells were treated with 100 ng/ml mouse or human interferon-γ (R&D System, Wiesbaden, Germany), or 10 ng/ml mouse or human TNF (R&D System) or with a combination of mouse and human interferon-γ (50-100 ng/ml) and mouse or human TNF (0.1-10 ng/ml) for 2 to 6 days. The β-cancer cells were identified by means of immunofluorescence using an anti-synaptophysin antibody (undiluted; Lifespan Biosciences, Seattle, Wash., USA).
Knock-Down of p16$^{Ink4a}$:

5×10$^4$ β-tumor cells were seeded in cell culture plates. After 72 h, the cells were transfected with 2 ml cell culture supernatant that contained sh-control or shp16/19 Mscv vectors, in presence of 1 μg/ml polybrene (Sigma, Munich, Germany) for a total transduction time of 12 h. After 5 days, the transduced cells were selected by treatment with 1 μg/ml puromycin (Sigma) for 72 h. The transduction rate was determined by counting GFP-positive cells under a Zeiss Axiovert 200 microscope (Zeiss, Oberkochen, Germany) and was usually >90%.
In Vitro Proliferation Assays:

After the treatment as described above, the proliferation of the cancer cells was measured either by means of [$^3$H]-thymidine incorporation or by a BrdU-based cell proliferation ELISA or by the XTT-based cell proliferation kit II according to manufacturer's instructions (Roche Diagnostics, Mannheim, Germany).
In Vitro Growth Arrest Assays:

The different cancer cells were seeded with a density of 1×10$^4$ cells/cm$^2$. Then, the cells were treated either with control medium or cytokines, as described above, for 4 to 5 days. After the treatment, the cells were trypsinized, and the living cells were counted with a Zeiss Axiovert 25 microscope (Zeiss, Oberkochen, Germany) using a Neubauer counting chamber (Karl Hecht GmbH, Sondheim, Germany). The cells were again seeded with 2×10$^4$ cells/cm$^2$ and cultivated in complete RPMI 1640 medium in absence of the cytokines, until the control cultures achieved confluency. Thereafter, the cells were trypsinized, counted, and again seeded (see also FIG. 13: Method for screening substances). After passage 1-2, 1,000 to 3,000 living cells were seeded on Multiscreen™ HTS 96-well filtration plates (Millipore, Billerica, USA), and the proliferation was measured by means of the BrdU-based cell proliferation ELISA in combination with the Vector® SG substrate kit for peroxidase (Vector Laboratories, Burlinggame, USA), in order to visualize the BrdU-incorporating cells. The BrdU-positive spots were counted with an ELISPOT reader (BIO-SYS, Karben, Germany).
Treatment of Mice with Tag-$T_H1$ Cells:

Before the first Tag-$T_H1$ cell-based therapy, all mice were irradiated. Then, 1×10$^7$ Tag-$T_H1$ cells were intraperitoneally injected once a week (beginning: week 6 of life) in 0.9% NaCl solution (Tag-$T_H1$) or NaCl solution alone (sham). In general, the mice were killed after 6 weeks of treatment (week 12 of life).
Transfer of β-Cancer Cells into Immunodeficient Mice:

β-cancer cells that were isolated from different mice groups, were cultivated for 3 passages. Then, 10 to 60% of the β-cancer cells were subcutaneously injected into immunodeficient NOD-SCIDxIL2Rcγ$^{-/-}$ mice. The tumor growth was monitored with a measuring rod and the blood glucose levels were measured with an Accu-Check Sensor (Roche Diagnostics) for 7 weeks.
Immunofluorescence and Immunohistochemistry for Investigating the Senescence and Re-Differentiation:

The different cancer cells were cultivated on culture slides (BD Biosciences, Heidelberg, Germany). After the treatment, the cells were fixed 1:1 with acetone/methanol, and the culture slides were washed with PBS/0.05% Tween 20 at room temperature, blocked with serum-free DAKO block (DAKO, Hamburg, Germany), washed again and then incubated with the following antibodies: anti-PHP1γ (dilution 1:100; Abcam), anti-Ki67 (dilution 1:100; Abcam), anti-p16Ink4a (dilution 1:100; Santa Cruz Biotechnologie) or anti-glucose transporter2 (anti-Glut2; dilution 1:1000; Abcam). After a washing step, the culture slides were incubated with anti-rabbit Alexa488 (Invitrogen), anti-rabbit Cy3 (Dianova, Hamburg, Germany), anti-mouse Alexa555 or anti-mouse Alexa488 (Cell Signaling Technology), washed again and then incubated with DAPI (Invitrogen). The analysis occurred using a Zeiss Axiovert 200 microscope and the Visiview Software (Visitron system, Pucheim, Germany).

SA-β-Galactosidase Activity Assay:

The cancer cells were fixed for 15 min at room temperature and then stained for 16 hours at 37° C. using the β-galactosidase staining kit (US Biological; Swampscott, USA). SAP-gal-positive and negative cells were counted using a Zeiss Axiovert 200 microscope.

Cell Cycle Analysis:

After treatment of the β-cancer cells, the cell cycle analysis was carried out by means of the BD Pharmingen FITC-BrdU Flow Kit according to manufacturer's instructions (BD Biosciences). The samples were analyzed by means of flow cytometry on a LSR II of Becton Dickinson (Heidelberg, Germany) and the following cell cycle phases in % of the total population were determined: subG$_1$ (apoptotic cells), G$_1$/G$_0$ (2n, BrdU-negative), S (2n-4n, BrdU-positive) and G$_2$/M phase (4n, BrdU-negative).

Western Blot for Investigating the Senescence and Re-Differentiation:

After the treatment, the cancer cells were disrupted in lysis buffer (50 mM Tris-HCl, pH 7.5, 150 mM NaCl, 1% Triton X-100, 0.5% SDS, 1 mM NaF, 1 mM Na$_3$VO$_4$, and 0.4% β-mercaptoethanol) that contains a protease inhibitor cocktail and a phosphatase inhibitor cocktail (PhosSTOP of Roche Diagnostics). After a protein determination with the Bicinchoninic Acid Assay (BCA; Thermo Fisher Scientific), the proteins were separated by a 12% SDS-PAGE or by means of pre-produced Mini Protean TGX Precast gels (4-15%; of BioRad), transferred on a PVDF membrane and blocked with 3% milk powder in TBS/0.1% Tween 20 (TBST). The membrane was then incubated with a anti-glucose transporter2 (anti-Glut2; dilution 1:1,000; Abcam), anti-Rb (Ab-780) (1:1,000), anti-Rb (phospho-Ser-795) (1:1,000; both antibodies of SAB Signalway Antibody, Pearland, Tex., USA) or anti-β-actin antibody (1:1,000; BioVision). After a washing step with TBST and following blocking of non-specific binding sites, the blots were incubated with a goat anti-rabbit horseradish peroxidase (HRP)-conjugated antibody (1:3,000; Cell Signaling Technology) and then washed again. Finally, the antibody binding was made visible with the ECL detection reagent (Amersham).

Array Comparative Genomic Hybridization (Array-CGH):

By means of comparative genomic hybridization (CGH), genome-wide quantitative chromosomal aberrations can be detected, as they are often found for solid tumors in the context of tumor progression and the associated genomic instability.

For this purpose, the DNA was isolated from the tumor tissue and marked with a fluorescence marker. In parallel, a control DNA of a healthy donor was marked with a second fluorescence marker. Both DNAs were then hybridized on a genome-wide array of 105,000 oligonucleotides. They now have bound proportionally to their relative content of the hybridization solution. From the binding behavior, the genome-wide DNA content of the tumor relative to the healthy genome could be calculated and shown in a graph. For the analysis, the Agilent Human Genome CGH 105A Micro-Array (Agilent Technologies, Boblingen, Germany) was used and measured at a DNA Microarray Scanner (Agilent Technologies). The obtained data were evaluated with the Software Feature Extraction 10.5.1.1 and DNA Analytics 4.0.85 (Agilent Technologies) based on the Human Genome Build 18.

Healing Test

In the context of a healing test, a patient was treated, upon his own wish, after complete explanation of any potential consequences, with a combination of IFN-α and TNF. The patient had a peritoneal carcinoma (primary tumor: melanoma) with strong ascites. His surviving prognosis was estimated to be 1-2 weeks. The treatment occurred by ascites punction and administration of IFN-α and TNF. During monitoring, it was found that the patient endogenously produced TNF already in sufficient amounts, so that in this case only IFN-α had to be administered.

Results

Figure 1B:
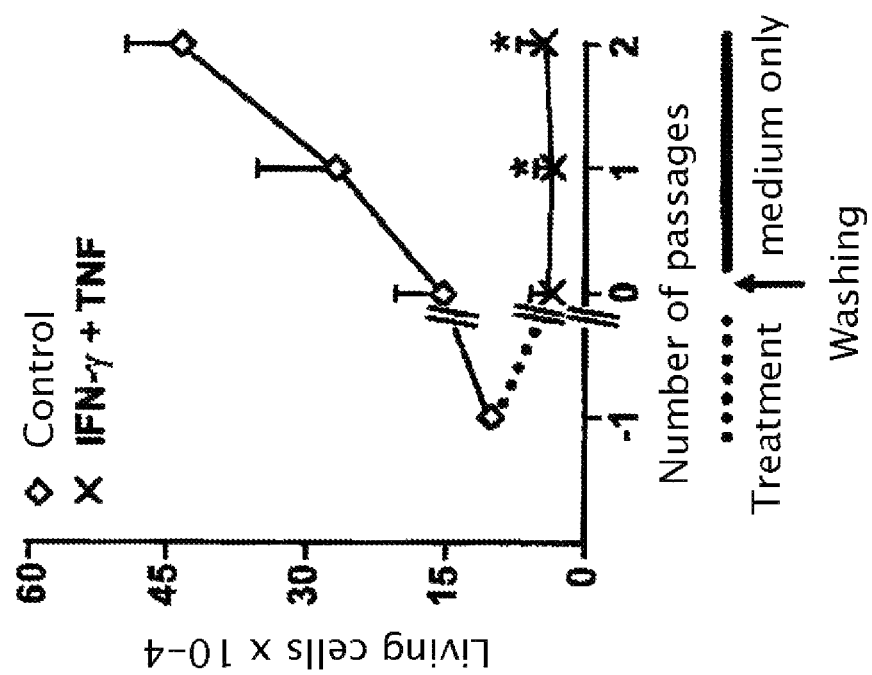
FIG. 1B shows cell cycle measurements on β-cancer cells that were untreated and treated with a combination according to the invention (STAT1 and TNFR1 activators). The β-cancer cells were not only arrested (A right-hand and B left-hand part of the illustration), but were also held in a continued permanent growth arrest after removal of the senescence-induced signals, according to definition.

From FIG. 1 can be taken the proof that the combination of substances that activate the STAT1 and TNF signaling pathways (here: interferon-γ and TNF) can induce in vitro a stable growth arrest of β-cancer cells. In FIG. 1a is shown a cell cycle analysis and the mean G$_1$/S ratio of β-cancer cells that were cultivated either in presence or in absence of interferon-γ and TNF. In FIG. 1b is shown the cell count of the living cells of β-cancer cells that were treated for 5 days with medium or with interferon-γ and TNF. Even after removal of the growth-inhibiting signals/cytokines that led to the activation of the STAT1 and TNFR1 signaling cascades, the cells continued to be stably arrested in the senescence (FIG. 1B period after washing).

It can be seen that the combined treatment caused that the growth of freshly isolated β-cancer cells was completely arrested in presence of interferon-γ and TNF, whereas the untreated cells quickly proliferated in the medium. From the cell cycle analysis can also be taken that more than 25% of the untreated β-cancer cells were in the S phase and 40% in the G$_1$/G$_0$ phase, which explains the fast proliferation thereof. The common activation of STAT1 and TNFR1/CD95 thus caused the arrest of the β-cancer cells in the G$_1$/G$_0$ phase within 3 days (see FIG. 1a). After 5 days the growth arrest was then permanent (FIG. 1b).

Figure 2:
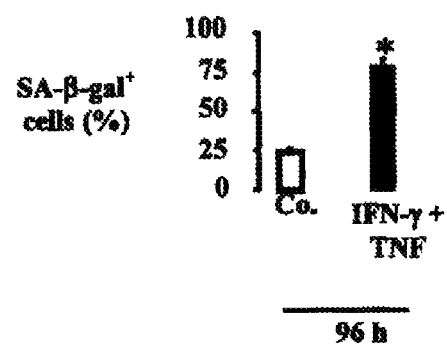
FIG. 2 shows the proof that a combination according to the invention of STAT1 and TNFR1 activators (here: interferon-γ and TNF) modified the senescence-associated β-galactosidase (SA-β-gal) activity in the tumor cells: The diagram shows that the combined administration of interferon-γ and TNF strongly induces the SA-β-gal activity in β-cancer cells.

From FIG. 2 can be taken that the combination according to the invention of STAT1 and TNFR1 activating signals, here interferon-γ and TNF, also induces the characteristic, senescence-associated markers, what is shown here by the proof of the senescence-associated β-galactosidase (SA-β-gal) activity. In the experiments was shown that within 3 days the combination according to the invention induced the early-senescence marker PHP1γ in 75% of the β-cancer cells and SA-β-gal in 50% of the cancer cells (not shown). After 4 days, finally, a stable growth arrest was induced, which could be shown by the late-senescence marker SA-β-gal in 80% of the cells (see FIG. 2).

FIG. 3 shows the results of the investigation of the cell proliferation after BrdU staining, wherein four different experiment approaches are shown: As explained above, the β-cancer cells were treated for 4 to 5 days either with medium (Co.), with STAT1 activating (interferon-γ) only, with TNFR1-activating (TNF) only, or with the combination of STAT1 and TNFR1/CD95-activating signals (interferon-γ and TNF). After the incubation, the cells were washed, trypsinized and then cultivated in absence of the cytokines for two additional passages. After passage 2, 3,000 living cells were seeded in 96-well plates, and the cell proliferation was analyzed by means of BrdU staining. It can be seen that only a combination of STAT1 and TNFR1-activating signals (interferon-γ and TNF), however neither the activation of STAT1 (interferon-γ) alone, nor the activation of TNFR1 (TNF) alone, could induce in vitro a stable growth arrest in isolated β-cancer cells. FIG. 3b shows the mean values of the BrdU-positive spots of the β-cancer cells after the treatment with medium, two weeks after the induction therapy with interferon-γ, TNF or the combination of interferon-γ and TNF.

Figure 4:
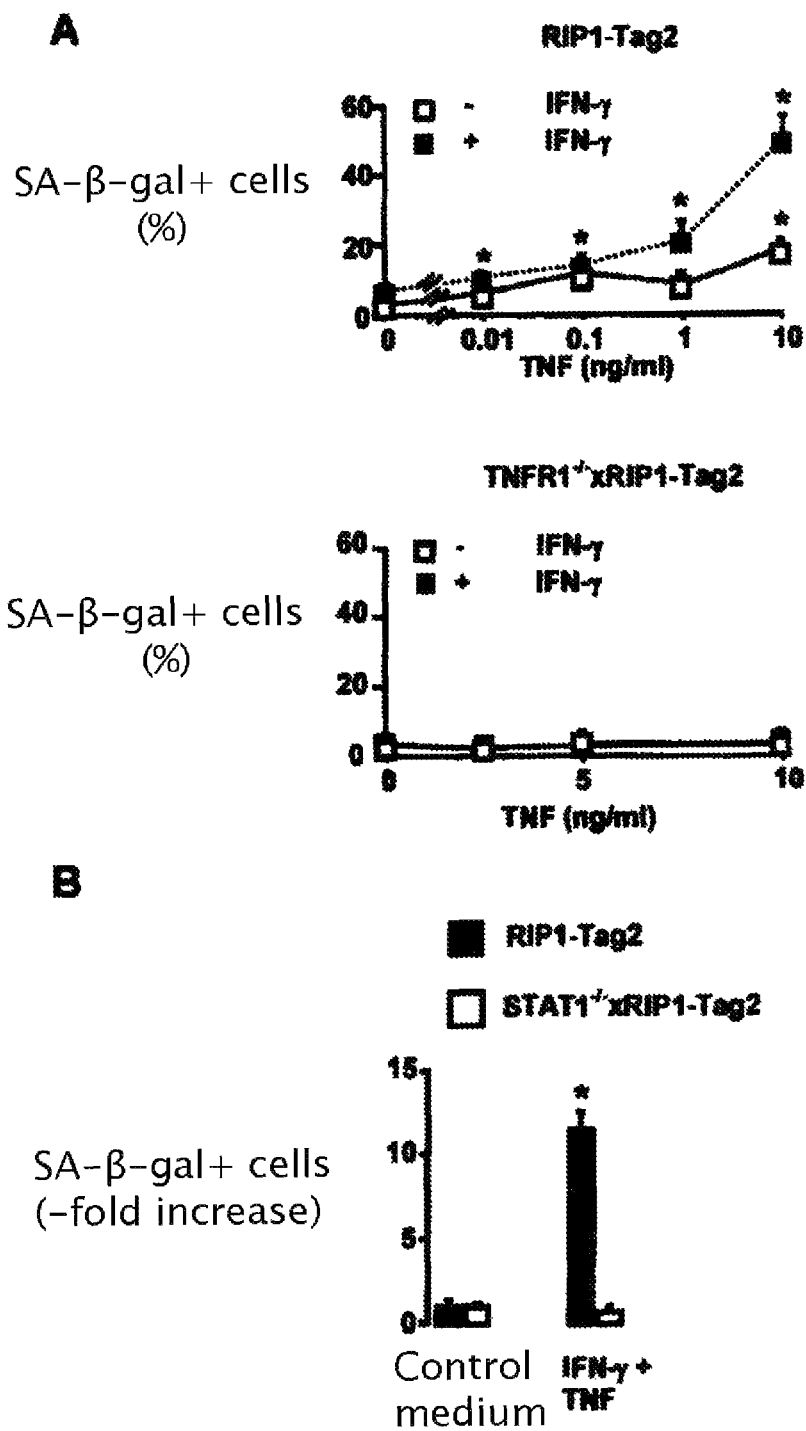
FIG. 4 shows the proof that for the induction of senescence by the combination of IFN-γ and TFN definitely the STAT1 and the TNFR1 signaling cascades must commonly be activated.

The results shown in FIG. 2 were further confirmed with the results shown in 4a and 4b, according to which in neither STAT1 nor TNFR1-deficient β-cancer cells, a senescence induction occurred by the combined application of interferon-γ and TNF, which again confirms that the two signaling chains STAT1 and TNFR1 are essential, or that the activation thereof is essential, in order to induce the senescence of tumor cells. The positive control for FIG. 4a is shown at top, the experiment is shown at bottom in FIG. 4a and shows that the combination of interferon-γ and TNF in TNFR1-deficient tumors also induces no senescence.

Figure 5:
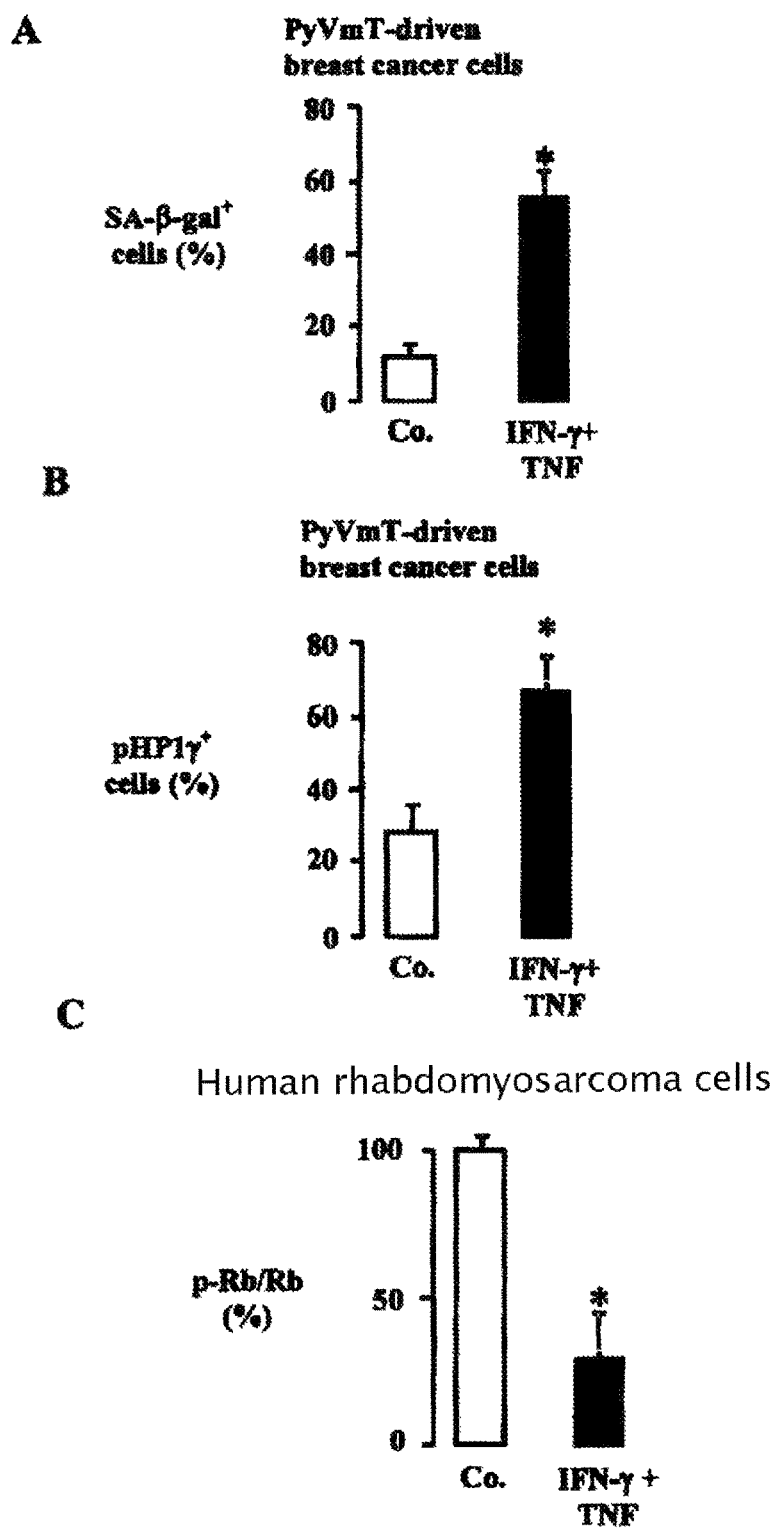
FIGS. 5A and 5B show the proof that a combined administration of two substances (here: interferon-γ and TNF) induces the senescence in breast cancer cells.
FIG. 5C shows the proof that a combined administration of two substances (here: interferon-γ and TNF) induces the senescence in breast cancer cells as well as for rhabdomyosarcoma cells of the human.

FIGS. 5a and 5b finally show the induction of the SA-β-gal activity and the mean percentage of senescent PHP1γ$^+$ cells in breast cancer cells that were isolated from transgenic mice, 72 hours after treatment with medium or with interferon-γ and TNF. Here, too, is shown that with a treatment with the combination according to the invention the two senescence markers (β-galactose activity and PHP1γ) have strongly increased, compared to the untreated cells. FIG. 5c shows exemplarily the change of the phosphorylation state of the cell cycle regulator Rb in rhabdomyosarcoma cells of the human that is normalized again by the IFN-γ and TNF treatment.

Figure 6A:
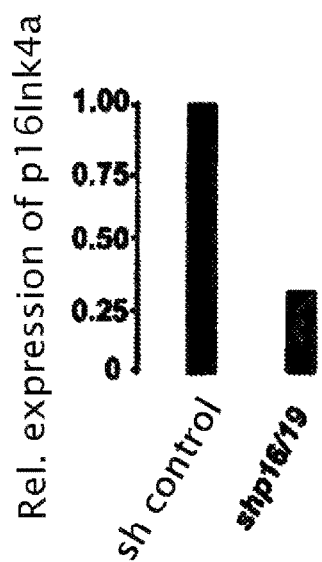
FIG. 6A shows the proof that the induction of senescence is strictly dependent on the presence of the p16$^{Ink4a}$ protein; electively in tumor cells, in which p16 was blocked by shRNA.

FIG. 6 shows that short hairpin p16/19(shp16/19) RNA regulates p16$^{Ink4a}$ down.

Figure 6B:
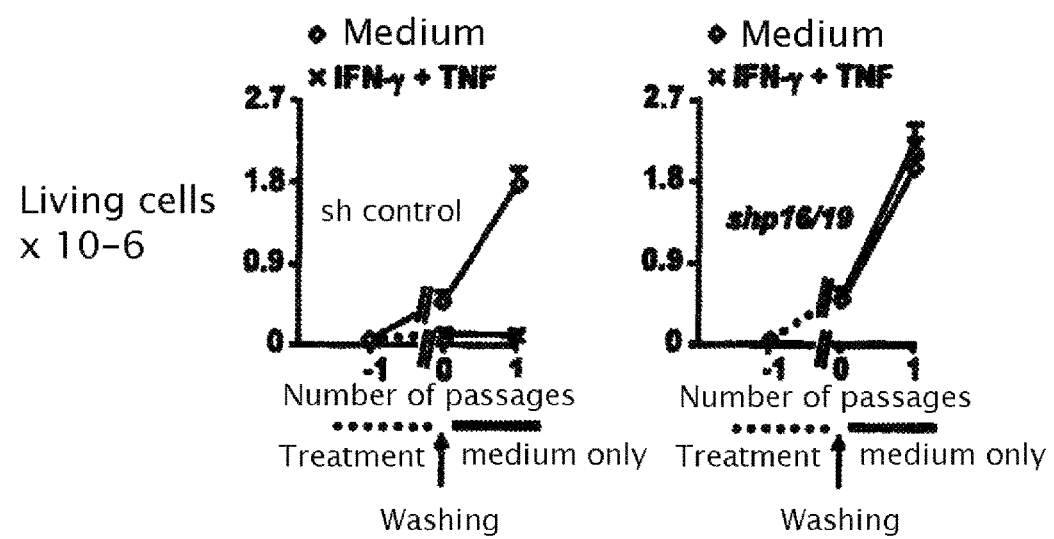
FIG. 6B shows the combination of interferon-γ and TNF cannot induce a senescence (right-hand illustration shp16 x symbol); this is in contrast to the induction of lysis, apoptosis or necrosis of tumor cells by IFN-γ and TNF.
Figure 7:
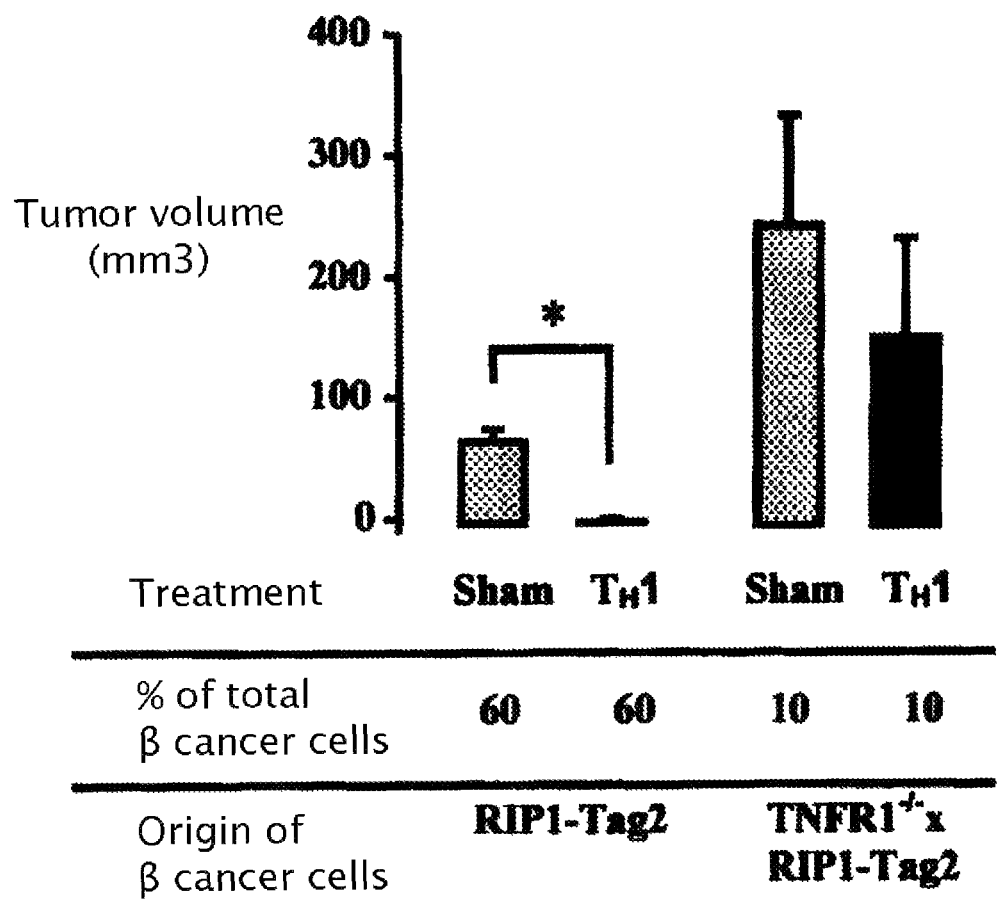
FIG. 7 shows the proof that the in vivo induced senescence lasts over months and is dependent on the presence of the TNFR1 on the tumor cells; depending on TNFR1, the immunotherapy in vivo leads to that the tumor cells are always arrested, even when they are transferred into immunocompromised mice; the senescent cells thus behaved, in spite of the expression of the tumor driver gene, as benign cells—and not as tumor cells anymore; this also illustrates for the first time in particular that hereby the tumor stem cells could be transferred into a permanent growth arrest.

FIG. 6b shows that cells that were transduced with control shRNA reacted normally to the treatment with IFN-γ and TNF and initiated a senescence-defining stable cell cycle arrest (left-hand diagram). In contrast, after a suppression of p16 by means of p16/19shRNA, the treatment with IFN-γ and TNF could not induce anymore a cell cycle arrest in the tumor cells. The cells proliferated quickly in an uninhibited manner in the presence of IFN-γ and TNF (right-hand diagram). This shows that p16$^{Ink4a}$ is indispensable for the IFN-γ and TNF-induced senescence. In FIG. 7, β-cancer cells were transduced with control shRNA or shp16/19 Mscv vectors, and then treated for five days with medium or with IFN-γ and TNF. Thereafter, the cells were washed, trypsinized and then further cultivated in absence of the cytokines. The mean value of the cell counts of living cells from three independent cultures is shown for the different passages p−1 to p1.

FIG. 7 shows the tumor volume in immunodeficient NOD-SCIDxIL2Rcγ$^{−/−}$ mice after transfer of $10^5$ β-cancer cells that originate from either placebo (sham) or Tag-T$_H$1-cells treated mice. In the table are shown the origin (from normal RIP1-Tag2 mice on the left or from TNFR1-deficient RIP1-Tag2 mice on the right) and the percentage of β-cancer cells/mouse transferred from the culture that were respectively injected. Since the TNFR1$^{−/−}$×RIP1-Tag2 cells proliferated more quickly in vitro, here only 10% of the isolated β-cancer cells obtained in vitro were transferred. FIG. 7 shows that the senescence mediated in vivo by T$_H$1 lymphocytes producing TNF and IFN-γ remains stable first in vitro for three passages and then, after a transfer of the senescent β-cancer cells, persists itself in vivo for at least 6 weeks, since exclusively in this group no detectable tumors grew in immunosuppressed mice. In contrast, the β-cancer cells of placebo-treated mice grow to form large tumors. In particular, the tumors grew quickly and were very large, when the tumor cells were isolated from TNFR1$^{−/−}$×RIP1-Tag2 mice. Here, too, the therapy with T$_H$1 cells had no effect, which again proves in vivo the dependence of the induction of senescence on the TNFR1 signaling pathway.

Figure 8A:
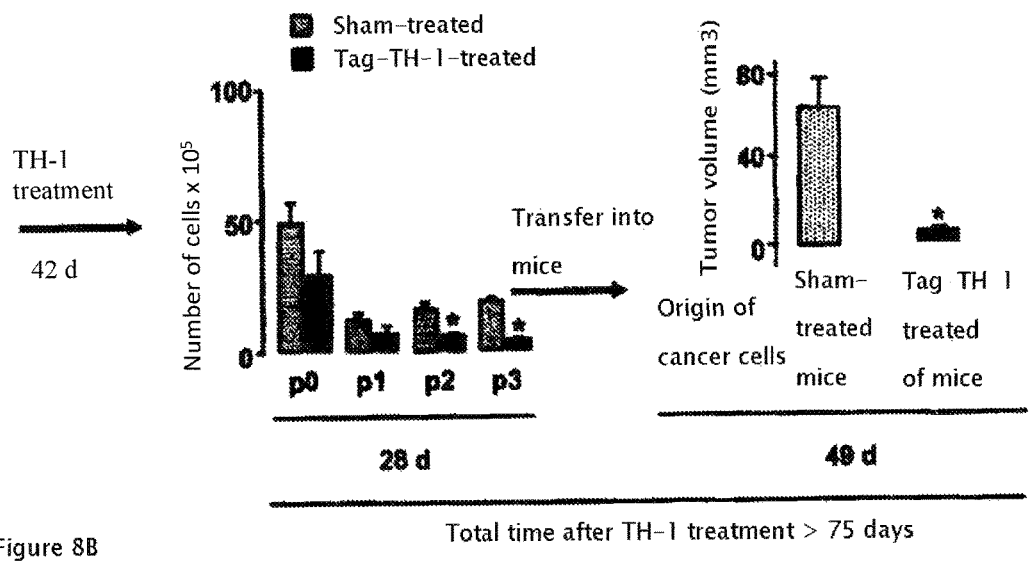
FIG. 8A shows the proof that a transplantation of arrested tumor cells in immunodeficient mice does not stop the tumor arrest and thus no tumor growth can be observed anymore (>75 days).

FIG. 8A demonstrates the growth arrest of the tumor cells after beginning the T$_H$1 treatment (IFN-γ and TNF-producing cells) for in total 17 weeks (119 days). There is no tumor growth after transfer into immunodeficient mice.

Figure 8B:
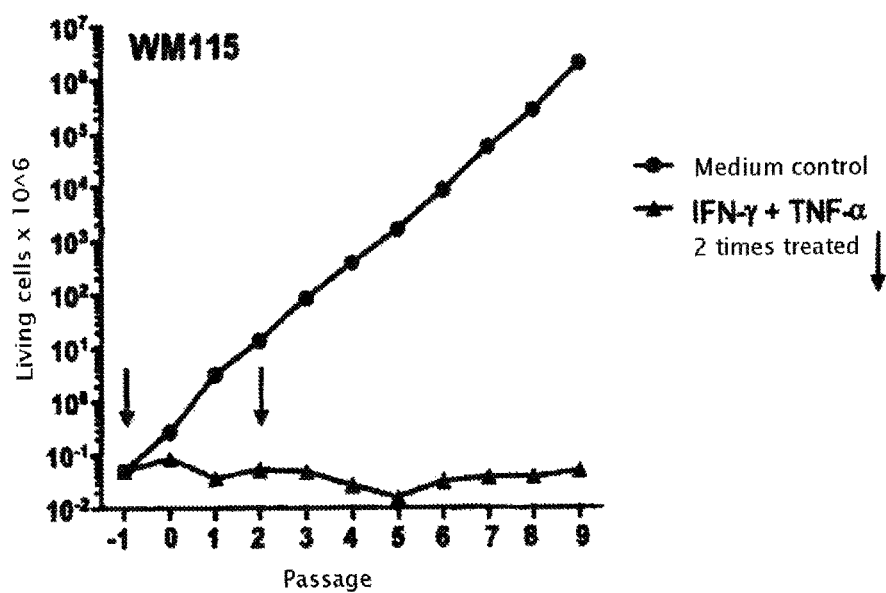
FIG. 8B shows the proof of the tumor arrest after treatment of WM115 melanoma cells with IFN-γ and TNF over 10 passages (>45 days).

FIG. 8B demonstrates the growth arrest of the melanoma cell line WM115 in vitro after beginning the IFN-γ and TNF treatment. The cells remained stable after in total 10 passages (i.e. >45 days).

Figure 9:
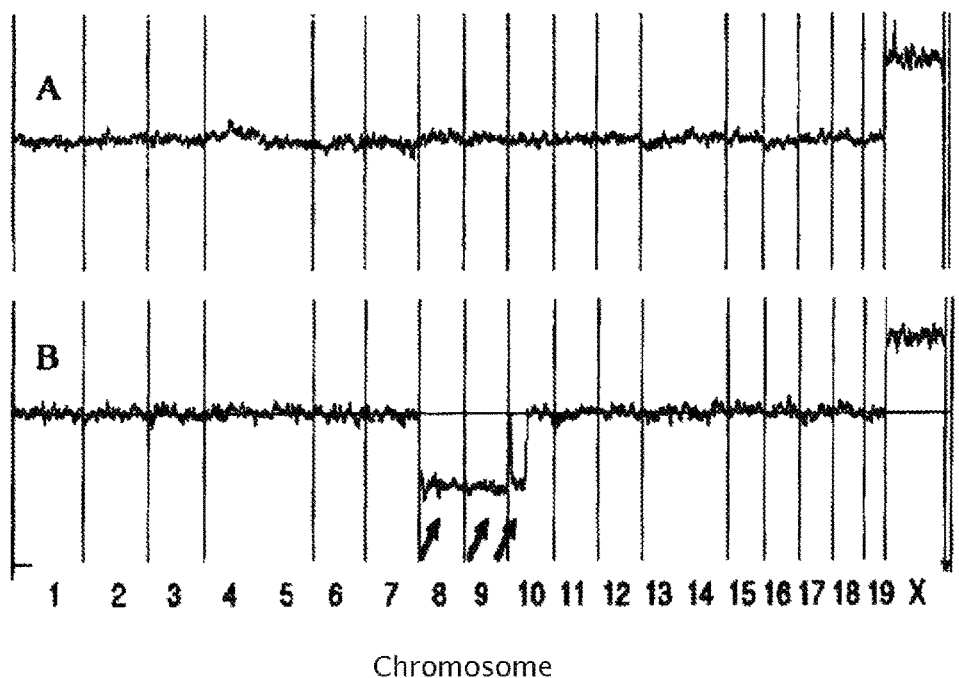
FIG. 9A shows the proof that the combined activation of STAT1 and TNFR1 stabilizes the genome of the tumor cells: The upper one of the two examples shows tumors from a treated animal without genome aberrations (in the CGH analysis).
FIG. 9B (the lower one of the two examples) shows tumors from a control animal of the same age given a sham treatment and having genome aberrations.

FIG. 9 shows that the adenoma-like tumors of Tag-T$_H$1 cells-treated RIP1-Tag2 mice remained genomically stable (FIG. 9A, blue line: CGH analysis without aberrations in the genome of the tumors from RIP1-Tag2 mice that were treated with tumor-specific T$_H$1 lymphocytes). In contrast, the CGH analysis of the β-cell tumors of placebo-treated mice shows several larger genomic deviations, such as, e.g., in FIG. 9B: a loss of the chromosomes 8 and 9 and parts of chromosome 10 (see black arrows). The X chromosome is used as a positive control.

Table 1 in FIG. 10 shows that different mouse cancer cell lines are driven by IFN-γ and TNF treatment into the senescence, i.e. into a permanent growth arrest that continues to exist even after completion of the actual treatment. Further, it can be taken from the table that for the induction of the permanent growth arrest, the simultaneous activation of the STAT1 and the TNFR1 signaling cascades was required.

For collecting the data of Table 1, the expression of the IFN-γ receptors IFNGR1 and IFNGR2, and of the TNF receptor TNFRSF1 in untreated cancer cell lines was determined by RT-PCR. The anti-proliferative effect was measured by cell count determination of the living cells at p0 after 4-5 days IFN-γ and TNF treatment. The permanent growth arrest was measured by cell count determination of the living cells at p1, 3-4 days after removal of IFN-γ and TNF and expansion in medium. The data are shown as mean value±S.E.M. of three independent cultures (see Table 1 in 9: gray=responder; white=non-responder; *determined by measurement of the SA-β gal). The non-responders either have a proven defect in the STAT1 or in the TNFR1-signal transduction.

Table 2 in FIG. 11 shows that different human cancer cell lines could also be transferred by IFN-γ and TNF treatment into the senescence, i.e. into a permanent growth arrest that continues to exist even after completion of the actual treatment. For collecting the data in Table 2, the expression of the IFN-γ-receptors IFNGR1 and IFNGR2, and of the TNF receptors TNFRSF1 in untreated cancer cell lines was determined by RT-PCR. The anti-proliferative effect was measured by cell count determination of the living cells at p0 after 4 days IFN-γ and TNF treatment. The permanent growth arrest was measured by cell count determination of the living cells at p1, 3-4 days after IFN-γ and TNF removal and culture with pure medium. The data are shown as mean value±S.E.M. of three independent cultures.

Table 3 in FIG. 12 shows that different freshly isolated malignomas/tumors of the human could also be transferred by IFN-γ and TNF treatment into the senescence, i.e. into a permanent growth arrest that continues to exist even after completion of the actual treatment. For collecting the data in Table 3, freshly isolated melanomas and sarcomas were used: Two human rhabdomyosarcoma and 4 human melanoma tumor cell preparations were directly isolated from patients. The isolation of the tumor cells from patient material was approved by the local ethics committee. The cell culture was made as mentioned above under Methods.

The anti-proliferative effect on primary human tumor cells (melanomas TüMel75, TüMe174H, ZüMel1H, or ZüMel, and sarcomas SRH, ZCRH) was measured by that living cells were counted after 4 (melanoma cells) or 12 days (rhabdomyosarcoma cells) of IFN-γ and TNF treatment. SRH, TüMel75, TüMel74H, ZüMel1H, or ZüMel1 were each treated with 100 ng/ml IFN-γ and 10 ng/ml TNF. ZCRH tumor cells were treated with 10 ng/ml IFN-γ and 1 ng/ml TNF. The growth arrest was determined by that living cells were counted 4 (melanoma cells) or 10 days (rhabdomyosarcoma cells) after IFN-γ and TNF removal. The data show a representative experiment of 3 independent experiments (SRH and ZCRH) or the mean value±S.E.M. of three independent cultures (TüMel75, TüMel74H, ZüMel1H, and ZüMel1; see Table 3 in FIG. 11: gray=responder; white=non-responder). For the tumor cells ZCRH and TüMel74H, the stable growth arrest was combined with cytotoxic effects.

FIG. 13 shows that isolated, completely de-differentiated β-cancer cells re-differentiate in presence of the $T_H1$ cytokines IFN-γ and TNF. This is shown by that after the therapy de-differentiated β-cancer cells even express again the late β-cell differentiation marker glucose transporter2 (Glut2) and were thereby transformed back into functional islet cells. This was shown by immunofluorescence (FIG. 13a) as well as by Western blot (FIG. 13b). Cell nuclei are shown in blue (FIG. 13a), and β-actin was used as a charge control for the Western blot (FIG. 13b).

Figure 14:
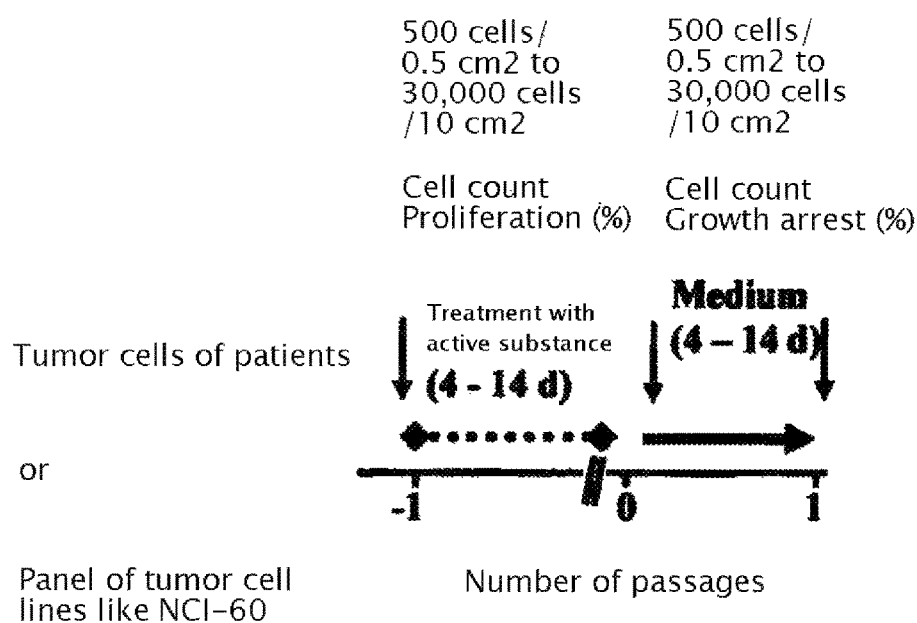
FIG. 14 shows an embodiment as proof of the occurred induction of senescence.

FIG. 14 shows a scheme of an embodiment (the mentioned cell counts are examples, but are not binding), by means of which the induction of senescence could clearly be proven. The cancer cells are seeded at passage −1 in a defined cell density and are then treated for 4-14 days with a combination of active substances. Thereafter, the cancer cells are harvested and counted, and seeded again in the same cell density in absence of the active substances. The determination of the permanent growth arrest (senescence) occurs in passage +1, approximately 4-14 days after the removal of the active substances. The experimental conditions have to be adjusted such that the control cell populations are not confluent and are thereby transferred into a growth arrest. By automated cell counting, this method can be used in the high-throughput method.

Figure 15A:
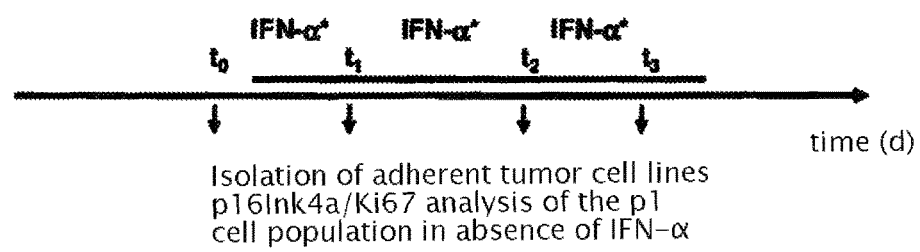
FIG. 15A shows that at the times t0, t1, and t3, adherent cells are isolated from the ascites liquid and grown on cell culture plates.

FIG. 15a shows the treatment scheme and the results of the healing test with IFN-α and TNF. At the times t0, t1, t2, and t3, ascites is taken. After the first taking (t0), the patient is treated with IFN-α. At the times t0, t1, and t3, adherent cells are isolated from the ascites liquid and grown on cell culture plates.

Figure 15B:
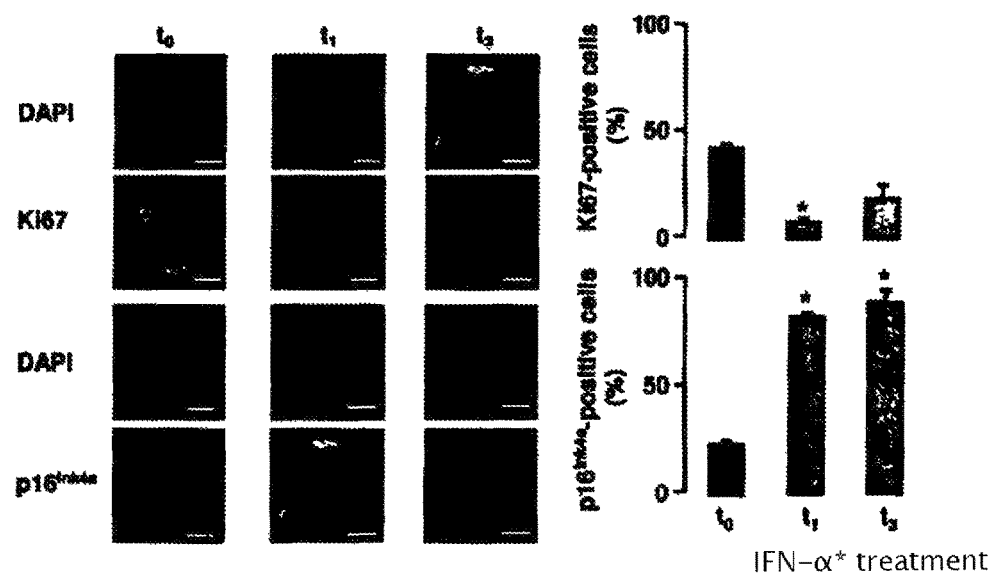
FIG. 15B shows at the times t0, t1, and t3, the senescence marker p16$^{Ink4a}$ and the proliferation marker Ki67 are determined by immunofluorescence microscopy. While KI67 decreases, there is a strong induction of p16$^{Ink4a}$ after in vivo cytokine treatment.

FIG. 15b shows further data of the same healing test: At the times t0, t1, and t3, the senescence marker $p16^{Ink4a}$ and the proliferation marker Ki67 are determined by immunofluorescence microscopy. While KI67 decreases, there is a strong induction of $p16^{Ink4a}$ after in vivo cytokine treatment.

At the time of the present application, the patient is already living more than 6 months (original surviving prognosis 1-2 weeks) in a relatively stable state. The mobility has increased to 90% (from originally 30%), he could take walks again (originally he was bedridden).

Figure 16:
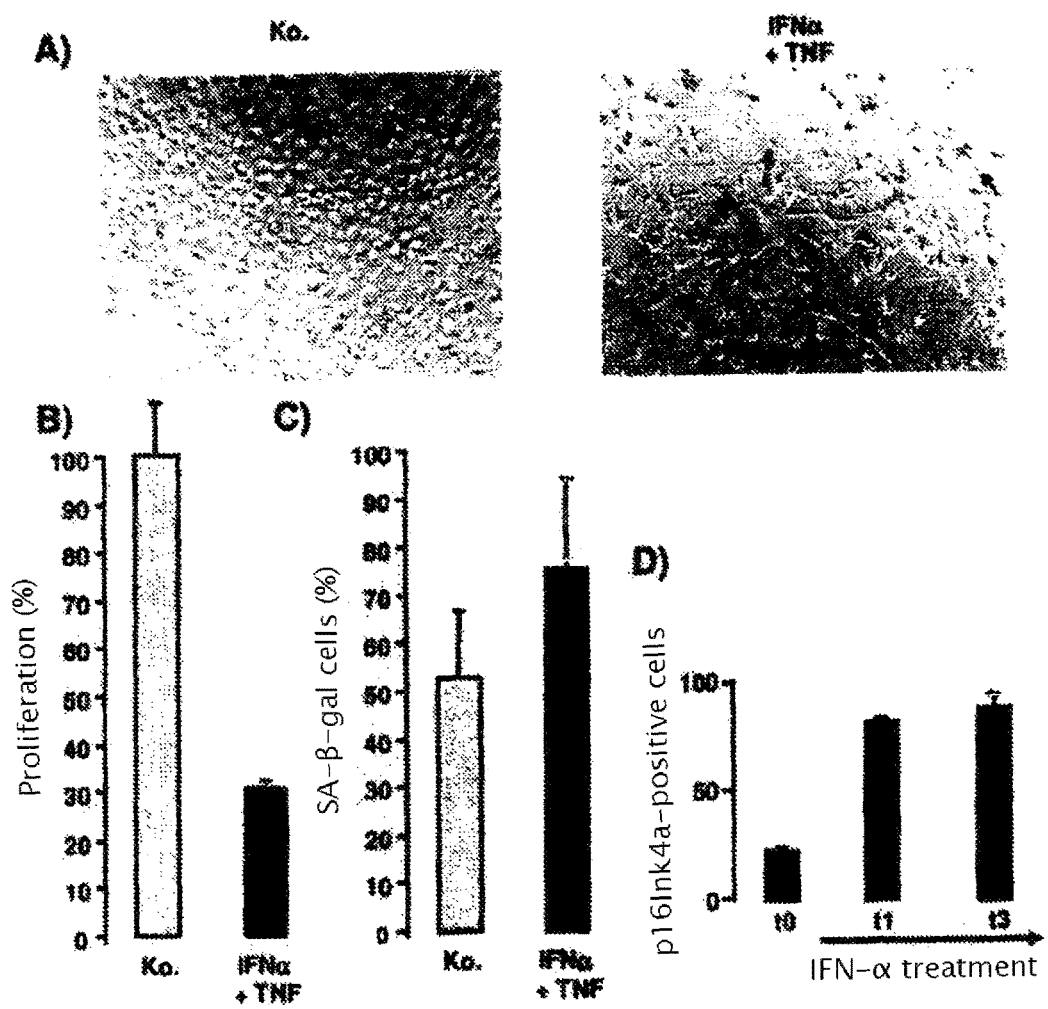
FIG. 16 A shows further results of the healing test: The tumor cells treated with IFN-α and TNF change in number and morphology.

FIG. 16: (A) IFN-α plus TNF induce senescence in primary tumor cells of a patient with peritoneal carcinosis: In particular the treatment with IFN-α plus TNF leads to clearly less tumor cells compared to the control (Co.) that in addition assume a neurites-like (arrows) or fried egg-like (broken line) morphology. (B) IFN-α plus TNF-treated tumor cells are strongly inhibited in their proliferation. (C) The activity of the senescence-associated β-galactosidase (SA-β-gal) increases after IFN-α plus TNF to more than 70%. (D) The corresponding tumor cells show a very strong expression of the senescence marker $p16^{Ink4a}$.

The invention claimed is:

1. A method of treating a tumor in a patient by inducing a growth arrest (senescence) in said tumor comprising the step of applying a therapeutically effective amount of a combination of two substances to said patient, in which $p16^{Ink4a}$ is expressed in the tumor cells of said tumor, wherein the two substances are a combination of interferon-gamma (IFN-γ) with tumor necrosis factor-alpha (TNF-α) or a combination interferon-alpha (IFN-α) with tumor necrosis factor-alpha (TNF-α), and wherein the induction of the senescence requires a treatment of the tumor cells for at least three to four days.

2. The method according to claim 1 wherein the tumor cells are premalignant or malignant, bona fide tumor cells, and/or tumor stem cells.

3. The method according to claim 1, wherein the application of said substance combination occurs for a period of time of at least 1 day to at most 30 days.

4. The method according to claim 1, the application of said substance combination is repeated every 3 to 6 weeks for a total time of two years.

5. The method according to claim 1, wherein said substance combination is applied to said patient topically, intratumorally, peritumorally, systemically, or percutaneously.

6. The method according to claim 1, wherein said substances of said substance combination are each employed in a concentration from 0.0001 ng/ml to 10,000 ng/ml in a pharmaceutical composition at the tumor cell.

7. The method according to claim 1, wherein the tumor is selected from HPV-induced benign tumors, precanceroses, carcinomas, in particular carcinomas of the skin, mucosae, lung, prostate, breast, ovaries, sarcomas, melanomas, CNS tumors or lymphomas/leukemias.

8. The method according to claim 7, wherein said substance combination is applied to said patient topically, intratumorally, peritumorally, systemically, or percutaneously.

9. The method according to claim 7, in which said substances of said combination are each employed in a concentration from 0.0001 ng/ml to 10,000 ng/ml in the pharmaceutical composition at the tumor cell.

* * * * *